United States Patent
Broadley et al.

(10) Patent No.: US 9,789,543 B2
(45) Date of Patent: Oct. 17, 2017

(54) PRESSURE FORMING OF METAL AND CERAMIC POWDERS

(75) Inventors: Mark W. Broadley, Downingtown, PA (US); James Alan Sago, Solon, OH (US); Hao Chen, Ann Arbor, MI (US); Edward J. Schweitzer, Cannonsburg, PA (US); John Eckert, Boyertown, PA (US); Jeffrey M. Farina, Zionsville, PA (US)

(73) Assignee: Accellent Inc., Wilmington, MA (US)

( * ) Notice: Subject to any disclaimer, the term of this patent is extended or adjusted under 35 U.S.C. 154(b) by 1269 days.

(21) Appl. No.: 13/695,397

(22) PCT Filed: Apr. 30, 2010

(86) PCT No.: PCT/US2010/033266
§ 371 (c)(1),
(2), (4) Date: May 9, 2013

(87) PCT Pub. No.: WO2011/136810
PCT Pub. Date: Nov. 3, 2011

(65) Prior Publication Data
US 2013/0218281 A1    Aug. 22, 2013

(51) Int. Cl.
*C22C 1/08* (2006.01)
*B22F 3/12* (2006.01)
(Continued)

(52) U.S. Cl.
CPC .................. *B22F 3/12* (2013.01); *A61F 2/30* (2013.01); *A61F 2/4425* (2013.01);
(Continued)

(58) Field of Classification Search
None
See application file for complete search history.

(56) References Cited

U.S. PATENT DOCUMENTS

| 3,888,663 A | 6/1975 | Reichman |
| 5,846,664 A | 12/1998 | Third |

(Continued)

FOREIGN PATENT DOCUMENTS

WO    2008-063526    *    5/2008

OTHER PUBLICATIONS

PCT International Search Report and PCT Written Opinion dated Jul. 1, 2010 for International PCT Application No. PCT/US10/33266 filed Apr. 30, 2010.

*Primary Examiner* — Jessee Roe
*Assistant Examiner* — Ngoclan T Mai
(74) *Attorney, Agent, or Firm* — Michael F. Scalise; Ganz Pollard, LLC

(57) ABSTRACT

A method of pressure forming a brown part from metal and/or ceramic particle feedstocks includes: introducing into a mold cavity or extruder a first feedstock and one or more additional feedstocks or a green or brown state insert made from a feedstock, wherein the different feedstocks correspond to the different portions of the part; pressurizing the mold cavity or extruder to produce a preform having a plurality of portions corresponding to the first and one or more additional feedstocks, and debinding the preform. Micro voids and interstitial paths from the interior of the preform part to the exterior allow the escape of decomposing or subliming backbone component substantially without creating macro voids due to internal pressure. The large brown preform may then be sintered and subsequently thermomechanically processed to produce a net wrought microstructure and properties that are substantially free the interstitial spaces.

74 Claims, 18 Drawing Sheets

(51) Int. Cl.

| | | |
|---|---|---|
| *A61F 2/44* | (2006.01) | |
| *B22F 7/06* | (2006.01) | |
| *B28B 1/24* | (2006.01) | |
| *C04B 35/111* | (2006.01) | |
| *C04B 35/486* | (2006.01) | |
| *C04B 35/50* | (2006.01) | |
| *C04B 35/505* | (2006.01) | |
| *C04B 35/632* | (2006.01) | |
| *C04B 35/634* | (2006.01) | |
| *C04B 35/636* | (2006.01) | |
| *C04B 35/638* | (2006.01) | |
| *C04B 35/645* | (2006.01) | |
| *B22F 3/02* | (2006.01) | |
| *B22F 3/24* | (2006.01) | |
| *B22F 7/00* | (2006.01) | |
| *B22F 7/02* | (2006.01) | |
| *B22F 7/08* | (2006.01) | |
| *A61F 2/30* | (2006.01) | |
| *C22C 1/04* | (2006.01) | |
| *C22C 33/02* | (2006.01) | |
| *A61F 2/32* | (2006.01) | |
| *A61F 2/38* | (2006.01) | |
| *A61F 2/40* | (2006.01) | |
| *A61B 17/70* | (2006.01) | |
| *A61B 17/80* | (2006.01) | |

(52) U.S. Cl.
CPC .............. *A61F 2/4455* (2013.01); *B22F 3/02* (2013.01); *B22F 3/24* (2013.01); *B22F 7/002* (2013.01); *B22F 7/008* (2013.01); *B22F 7/02* (2013.01); *B22F 7/062* (2013.01); *B22F 7/08* (2013.01); *B28B 1/24* (2013.01); *C04B 35/111* (2013.01); *C04B 35/486* (2013.01); *C04B 35/50* (2013.01); *C04B 35/505* (2013.01); *C04B 35/632* (2013.01); *C04B 35/636* (2013.01); *C04B 35/638* (2013.01); *C04B 35/63488* (2013.01); *C04B 35/6455* (2013.01); *A61B 17/7001* (2013.01); *A61B 17/80* (2013.01); *A61F 2/30767* (2013.01); *A61F 2/30942* (2013.01); *A61F 2/30965* (2013.01); *A61F 2/32* (2013.01); *A61F 2/38* (2013.01); *A61F 2/40* (2013.01); *A61F 2/446* (2013.01); *A61F 2/4465* (2013.01); *A61F 2002/3093* (2013.01); *A61F 2002/30578* (2013.01); *A61F 2002/30649* (2013.01); *A61F 2002/30677* (2013.01); *A61F 2002/30968* (2013.01); *A61F 2002/30986* (2013.01); *A61F 2002/4475* (2013.01); *A61F 2310/00017* (2013.01); *A61F 2310/00023* (2013.01); *A61F 2310/00029* (2013.01); *A61F 2310/00071* (2013.01); *A61F 2310/00101* (2013.01); *A61F 2310/00137* (2013.01); *A61F 2310/00185* (2013.01); *A61F 2310/00203* (2013.01); *A61F 2310/00239* (2013.01); *B22F 2998/10* (2013.01); *B22F 2999/00* (2013.01); *C04B 2235/5436* (2013.01); *C04B 2235/604* (2013.01); *C04B 2235/6021* (2013.01); *C04B 2235/6022* (2013.01); *C04B 2235/77* (2013.01); *C22C 1/0433* (2013.01); *C22C 1/0458* (2013.01); *C22C 33/02* (2013.01); *Y10T 428/12042* (2015.01); *Y10T 428/12153* (2015.01); *Y10T 428/24997* (2015.04); *Y10T 428/249921* (2015.04)

(56) References Cited

U.S. PATENT DOCUMENTS

| | | | |
|---|---|---|---|
| 6,022,509 A * | 2/2000 | Matthews | A61F 2/30942 264/44 |
| 6,027,826 A | 2/2000 | Derochemont | |
| 6,759,044 B1 * | 7/2004 | Petersen | C07K 14/44 424/139.1 |
| 7,674,426 B2 * | 3/2010 | Grohowski, Jr. | A61F 2/30767 419/2 |
| 2004/0092818 A1 | 5/2004 | Weaver | |
| 2004/0096350 A1 | 5/2004 | Moxson | |
| 2006/0129240 A1 * | 6/2006 | Lessar | A61F 2/4425 623/17.14 |
| 2007/0178005 A1 | 8/2007 | Broadley | |
| 2012/0136400 A1 * | 5/2012 | Julien | A61F 2/28 606/86 R |

\* cited by examiner

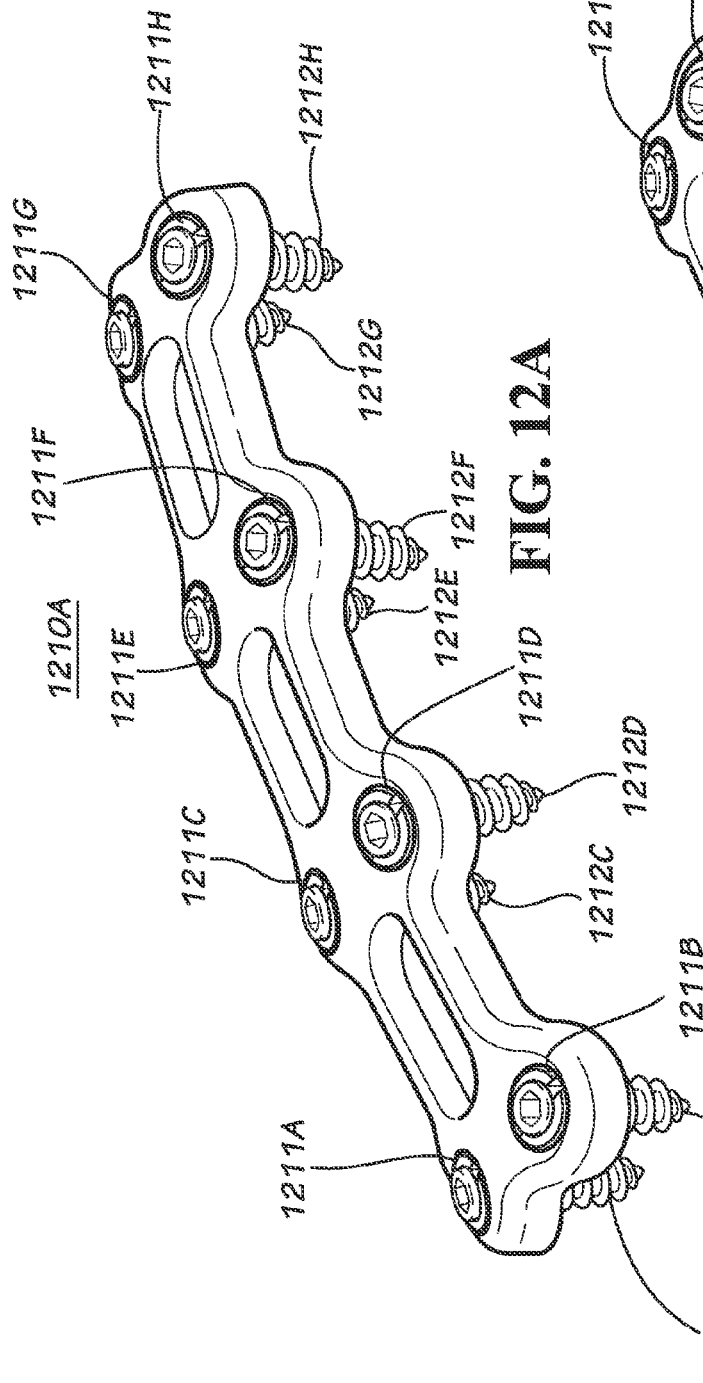
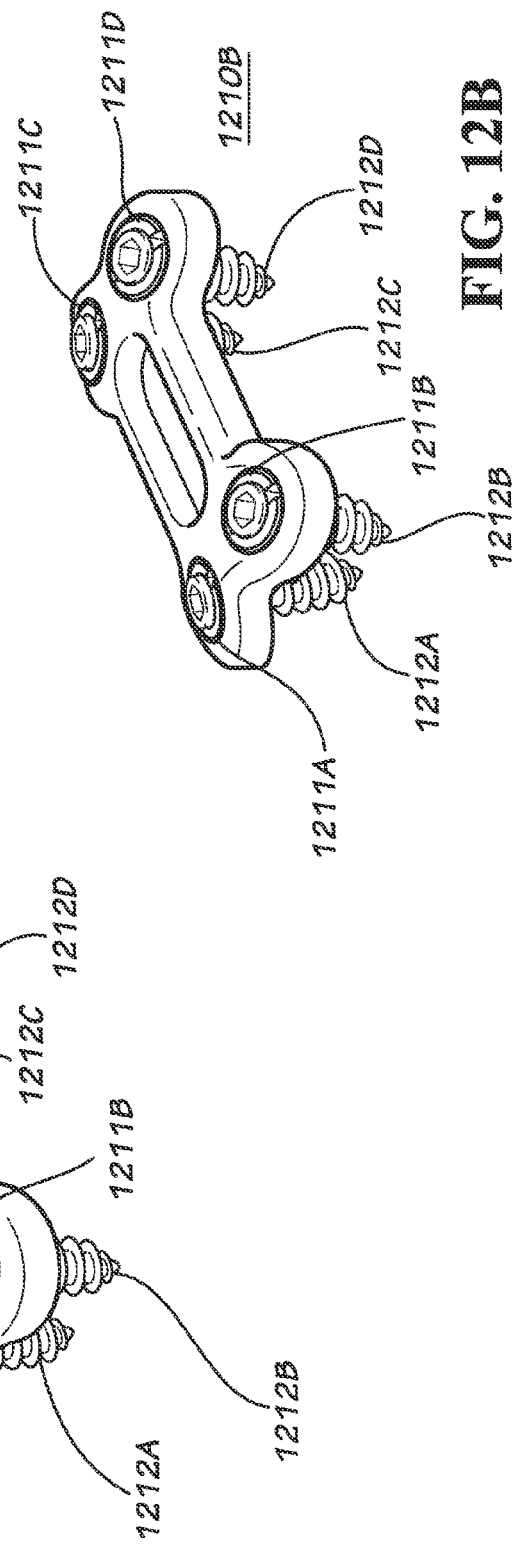
FIG. 12A
FIG. 12B (Forged and Annealed Wrought Material)

(As Sintered)

(Forged to 30% Reduction)

(Forged to 30% Reduction and Annealed)

PRESSURE FORMING OF METAL AND CERAMIC POWDERS

BACKGROUND

The inventive subject matter generally relates to methods of powder metal processing and articles made therefrom. The techniques may also be used in forming parts from ceramic powders or ceramic and metal powder compositions. Certain embodiments of the inventive subject matter relate to methods of direct compression molding in conjunction with secondary forming operations. Certain embodiments relate to comolding or overmolding of parts using different powder composition to form different portions. Certain embodiments relate to powder metal processing to form implantable medical components.

Traditional metalworking techniques have been used historically to make medical components. The cost of machining medical components increases significantly when the parts have complex geometries. Complex geometries have many features with precise shapes and dimensional tolerances.

Metal injection molding (MIM) is a net-shape injection molding process for producing metal parts. Medical parts, such as orthopedic components made of forged wrought metal cost more than similar MIM components. Forging of complex shapes from wrought metal simple geometric shapes requires high forging forces and stroke lengths and/or multiple blows. Machining of forgings to net shape can result in excessive machining cost and metal yield loss if the forging is larger than it needs to be. MIM techniques are therefore being developed for the medical and other industries that need relatively small and complex parts. MIM operations are well suited for producing small, highly complex geometries in many different alloys including stainless steels, alloy steels, and custom alloys. Design and economic limitations of traditional metalworking operations, such as machining, can be readily overcome by metal injection molding. MIM operations are especially suited for producing net and near net articles with close tolerances, and have been used to produce articles for the agricultural, automotive, medical, small appliance, and sporting goods industries, to name just a few.

In conventional MIM operations, fine metal powders are mixed with a polymer binder system to form a feedstock suitable for injection molding. The injection molding process and equipment are similar to that used in the art of injection molding of plastics. The geometric characteristics of the powder particles have a significant impact on the packing density, size and shape of interstitial micro voids, bulk flow during injection, debinding behavior, and microstructure development during later sintering stages. Traditional MIM powders are finer than 25 microns in size; in a few circumstances, the particles may be as large as about 40 microns. The metal powder and polymer binder mixture is forced through a gate into a mold, the part cools in the mold and the molded part is then ejected, thus producing a "green" part having at least the near-final shape but larger size than the desired finished article. Conventional MIM design parameters generally limit the thickness of the largest section of the molded parts to about 12 mm due to dimensional instability, and internal molding related macro void formation. The economics of large MIM parts is generally unfavorable due to the high cost of very fine metal powders and the long time required to remove binders from parts with large sections.

After molding, the "green" part is debound to produce a "brown" part. During conventional thermal debinding, the part is subjected to one or more heating cycles to decompose, or otherwise remove, the polymer binder. Thermal binder removal can take a minimum of several hours and is fraught with the risk of introducing deleterious flaws such as bloating or blistering. Rapid heat is generally avoided, especially if the binder content of the part is high, since this can lead to considerable pressure buildup inside the part, which can lead to catastrophic bursting. After debinding, the now "brown" part is sintered to facilitate consolidation," which results from metal-to-metal bond formation during sintering to create an interconnected mass of metal. During sintering, the part shrinks to its final size as a result of consolidation. The sintered part may be finished to the final shape using any number of processes, including but not limited to, coining, machining, grinding, cutting, polishing, or coating.

Conventional MIM operations are suitable for small parts with complex geometries to be made to net or near net shape in high volume. However, several technical difficulties arise when the part size increases or production volume decreases. For example, binder removal is a lengthy processing step that adds to the difficulty of MIM operations and becomes increasingly problematic as the size of the molded part, and hence the distance the binder must travel outwardly to be removed increases. Mold filling is also important so that empty corners, or other molding related macro voids, will not be left nor internal lamellar flaws introduced where the flowing composition layers join. Still further, handling, segregation, and bulk flow difficulties arise when providing larger quantities of feedstock during injection molding.

Thus, while MIM operations are capable of producing relatively small shaped articles in high volumes, these processes generally do not allow relatively larger parts (>12 mm in section thickness) to be made in a cost-effective manner. At lower production volumes, MIM operations are at a practical and economic disadvantage due to the relatively high cost of MIM molds. The as-sintered microstructure contains micro voids, and potentially, molding related macro voids that result in bulk densities less than or equal to 97% of theoretical alloy density. Microstructural features such as grain size are coarse and show little directionality when compared with wrought products. As a result, static and dynamic mechanical properties can approach but are not equivalent to the annealed properties of the wrought alloy.

Accordingly, it would be advantageous to have a cost-optimized process suitable for producing relatively large powder metal articles, of net or near net shape, having minimal internal voids in lower production volumes.

No matter what the size is, as-sintered parts produced from MIM and other pressure molding processes do not have the density, metallurgical structure, or mechanical properties provided by wrought materials for medical implant applications. Therefore, additional post-processing steps are needed to achieve wrought microstructures and properties.

Thus, there are a number of disadvantages and unfulfilled needs in the arts of MIM, and other metal forming techniques, such as forging, and casting. Among them are the following:

As-sintered powdered metal components processed by the cost effective MIM process do not have the density, metallurgical structure, or mechanical properties provided by wrought materials for medical applications, particularly surgical implant applications.

MIM traditionally has been limited to small parts (less than 12 mm thick) by the high cost of very fine metal powders and the difficulty in removing binders from parts with large sections.

Medical devices, such as implantable orthopedic components made of forged wrought metal cost more than similar MIM components.

Forging of near net shapes with complex geometries from wrought metal simple geometric shapes requires high forging forces and long stroke lengths and/or multiple blows.

Machining of forgings to near net shape can result in excessive machining cost and metal yield loss if the forging is larger than it needs to be.

Casting of large parts can result in shrinkage macro voids, microstructural segregation and coarse metallurgical structures.

Cast parts do not typically possess wrought mechanical properties.

Casting and forging of wrought materials do not easily allow for unitary parts or structures having zones with different metal compositions.

In view of the foregoing problems and disadvantages, there is a significant need for improved powder-metal forming ("PF") techniques to produce cost effective end products that are relatively large in size (versus traditional MIM) or complex in shape.

SUMMARY

In certain embodiments, the inventive subject matter provides methods and end products of pressure forming that overcome the problems and disadvantages in the prior art techniques.

In one possible embodiment, the inventive subject matter is directed to a method of molding a preform for a part that includes placing into a mold cavity for direct compression molding a feedstock in a weight or volume sufficient to form a large part. The feedstock includes: (i) a binder having a carrier component and a backbone component, the carrier component volatizing at temperatures under 750 degrees F., thereby creating micro voids and interstitial paths from the interior of the preform part to the exterior, which allow the subsequent escape of decomposing or subliming backbone component substantially without creating macro voids due to internal pressure; and (ii) a composition comprising a metal and/or ceramic powder. Pressure is applied to the mold to form a green preform. The green preform is debound by applying heat in a range of from about room temperature to about 750 F to substantially free the interstitial spaces of the carrier component to produce a large brown preform.

In another possible embodiment, the inventive subject matter is directed to a method of molding a preform for a part that includes: providing a composition in a weight or volume sufficient for forming a large part, the composition including at least one binder and at least one metal powder having particles of about 25 microns to about 150 microns. Introducing the composition into a direct compression mold having a shape or weight of a large part; providing at least one of a brown state insert or a green state insert to said mold; direct compression molding said composition about said at least one integral core such that said composition is co-molded or over-molded on said insert; and applying mold thermal management during said molding operation to produce a large green preform.

In another possible embodiment, the inventive subject matter is directed to a method of producing a preform for a part, that includes: providing a green or brown preform having: a first portion comprising a first metal and/or ceramic powder composition dispersed in a binder; one or more additional portions, at least one of which shares a boundary with the first portion, each additional portion comprising a metal and/or ceramic powder composition dispersed in a binder that is different from at least the first portion; and sintering the preform to bind the powder particles to each other to produce a consolidated, unitary preform that can be processed into a part.

In another possible embodiment, the inventive subject matter is directed to a method of pressure forming a preform for a part from metal and/or ceramic particle feedstocks, that includes: introducing into a mold cavity or extruder a first feedstock and one or more additional feedstocks or an insert made from a feedstock, wherein the different feedstocks correspond to the different portions of the part; pressurizing the mold cavity or extruder to produce a green preform having a plurality of portions corresponding to the first and one or more additional feedstocks; and debinding the preform into a brown preform.

In another possible embodiment, the inventive subject matter is directed to a green or brown unitary metal and/or ceramic preform for a part, the preform having: two or more portions consolidated by a pressure forming technique using feedstocks comprising (i) a metal and/or ceramic powder and (ii) a binder; and wherein each portion has a different composition and neither portion is a wrought portion, and wherein the brown state microstructure includes micro voids and interstitial paths characteristic of the volatilization of a carrier component of the binder.

In another possible embodiment, the inventive subject matter is directed to a consolidated unitary metal and/or ceramic part having two or more portions in the nature of a part consolidated by sintering a preform that is consolidated by a pressure forming technique using feedstocks comprising (i) a metal and/or ceramic powder and (ii) a binder; and wherein each portion has a different composition and neither portion is a wrought portion, and wherein the brown state microstructure includes micro voids and interstitial paths characteristic of the volatilization of the carrier component of the binder.

Additional advantages and novel features of the exemplary embodiments of the inventive subject matter will be set forth in part in the description, examples, and figures which follow, all of which are intended to be for illustrative purposes only, and not intended in any way to limit the invention, and in part will become apparent to those skilled in the art on examination of the following, or may be learned by practice of the invention.

These and other embodiments are described in more detail in the following detailed descriptions and the figures.

The foregoing is not intended to be an exhaustive list of embodiments and features of the inventive subject matter. Persons skilled in the art are capable of appreciating other embodiments and features from the following detailed description in conjunction with the drawings.

BRIEF DESCRIPTION OF THE DRAWINGS

The following figures show embodiments according to the inventive subject matter, unless noted as showing prior art.

FIGS. 5-12C show examples of "large part" implantable medical devices or components thereof.

DETAILED DESCRIPTION

Figure 1:
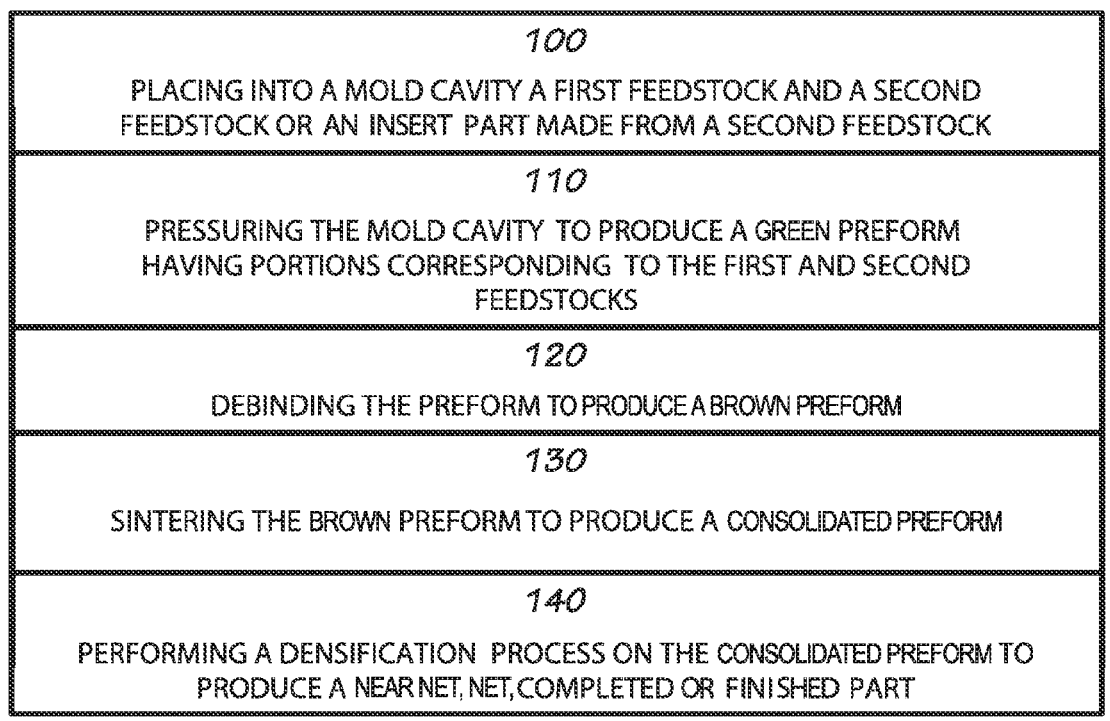
FIG. 1 shows a process map for producing molded parts having two or more portions derived from a first and one or more additional feedstocks.

Representative embodiments according to the inventive subject matter are shown in FIGS. 1-12C and 14-16.

The inventive subject matter pertains generally to the formation of metal parts and structures using a feedstock of powder metals that are dispersed in a moldable binder. The feedstock is used in a pressure molding process such as Metal Injection Molding (MIM) or Direct Compression (DC) molding (hereinafter, the term "pressure forming," or "PF" for short, will be used to refer to both MIM and DC processes). Typically, pressure forming involves pressures of about 500 to about 5000 PSI. The binder adds plasticity to the feedstock so that it can be pressure molded similar to non-metal polymer materials (plastic injection molding).

The inventive subject matter provides certain methods of direct compression molding particularly suited for the production of relatively large parts. As used herein "parts" means any article or object that comprises or is a portion of a functional device or other article of manufacture. As used herein, a part is a "large part" if it in whole or part meets at least one or more of the following three conditions: (1) it has a length greater than 4 inches along any dimension; it has as a volume greater than 200 gm of steel equivalent (equivalent allows for alternate materials with differing densities); or (3) it has dimensions such that it can contain a 12 mm diameter sphere (which dimensions may hereinafter be referred to as a 12 mm thickness.)

Certain embodiments of the inventive subject matter compression comold or overmold, injection comold or overmold, extrusion co-form or overform a metal and/or ceramic powder and binder composition, referred to herein as a "feedstock", to one or more inserts to the mold or extruder. As a result, a green part is created that consists of two or more portions of different compositions, at least two of which shares a boundary with each other. The green part is, then debound to create a brown part, which is sintered to produce a unitary consolidated preform for a part.

The preform made according to the inventive subject matter disclosed herein may be further densified by, for example, mechanical and/or thermomechanical processes into a net part or near net part that is completed in terms of final shape and dimension. The completed part may be further finished to provide additional attributes that do not substantially change shape and dimensions. Finishing operations, include, for example, polishing and texturing of surfaces.

The insert may be, for example, an integral core to produce a final or near final article. Another example is an extruded part that has a center portions and a surrounding portion or that has side by side portions, for example. Co-pending U.S. patent application Ser. No. 12/319,723, filed 12 Jan. 2009, which is hereby incorporated by reference in its entirety for all purposes, discloses pressure forming of feedstocks using extruders.

Certain embodiments further include mold thermal management providing preferred heating profile(s), cooling profile(s), or both during the molding operation. Still other embodiments facilitate the pressure molding of a preform that does not have the shape of the finished part that it will make. The as-sintered preform is subjected to at least one thermal, one mechanical, or one thermomechanical, forming operation to produce a densified near net or net part. These thermomechanical operations may include but are not limited to, hot isostatic pressing, cold isostatic pressing, uniaxial compression, biaxial compression, stamping, coining, forging, drawing, rolling, piercing, extrusion, upsetting, swaging, preheating and annealing.

In certain embodiments, at least one brown state core, green state core, or both, is provided to a direct compression mold. The arrangement of the core(s) within the mold cavity may be determined by any one or more of core size, core shape, desired final article shape, or desired final article properties. The core may be made of the same composition as the remainder of the article or may be made of a different composition with favorable properties such as higher strength or lower cost. Alternatively, the core may be made of the same composition but contain particles of a different size or alternate binders. The remaining mold cavity space is subsequently filled with a powder and binder composition. The composition comprises at least one metal powder having particles from about 2 microns to about 150 microns, preferably about 25 microns to about 150 microns, in size. In some embodiments, the inventive subject matter also contemplates the use of at least one ceramic powder composition. Generally the particles would have particles from about 2 microns to about 150 microns, preferably about 25 microns to about 150 microns, in size. These ceramic powders may include alumina particles, yttrium particles, lanthanum oxide particles, zirconia particles, or combinations thereof. Some embodiments contemplate blends of ceramic and metal particles. The ceramic powders can vary from 1 to 20% by weight for metallic products that require metallic surfaces with improved hardness and wear resistance, to 80 to 99% by weight for ceramic products with improved toughness. In blended compositions, the metal particles wet the ceramic particles such that there are islands of ceramic surrounded by metal.

Generally, any number of conventional binders may be used including, without limitation, acetal, polyethylene, polypropylene, polyethylene glycol, polyalkylene glycol, paraffin wax, oleic acid, polysaccharide (agar), polystyrene, naphthalene, paradichlorobenzene or combinations thereof. In some embodiments related to direct compression molding of larger parts, select binders are used, as described below.

Embodiments of the inventive subject matter provide several benefits over conventional MIM operations. For example, conventional MIM operations are optimized for small parts that have complex geometries and are produced in large quantities. In conventional MIM processes, however, poor mold filling, ineffective debinding, and numerous other issues can result in internal molding and debinding related macro void formation in larger sized articles. Certain embodiments of the herein disclosed inventive method direct compression molds about at least one integrated core in order to minimize the tendency for internal macro void formation for relatively large molded parts. In fact, use of a brown core also reduces the overall debinding time for the fabricated article, and minimizes the risk of internal blister formation due to incomplete debinding. Other embodiments include certain thermal management methods to facilitate mold de-gasing while minimizing macro void formation during the molding operation. For example, for molding large parts greater than 4 inches in diameter, there may be entrapment of gases. A thermal management profile for avoiding entrapped gases may be a heating of the mold and its contents from the bottom-up to create an upwardly moving liquid or plastic interface that drives out the upper surface of the mold contents. Internal defects, if any, can also be further mitigated by later thermomechanical forming operations. Articles made by the inventive methods disclosed and claimed herein provide various additional benefits including density and other material properties similar to those of wrought articles.

The PF process produces a "green" preform that still includes the binders. The carrier binder is removed in a first debinding process (typically a solvent, thermal, drying or reactive catalytic treatment), producing a "brown" part. The brown part is then heated to a temperature near the melting temperature of the metal particles so as to cause the metal particles to bind together, enabling the formation of a unitary metal structure. This step is known as sintering. For ceramics, the particles are also heated to near their melting temperature, which may be as high as or higher than 2400 degrees F.

The inventive subject matter provides certain methods of molding particularly suitable for the production of relatively large parts, but not limited thereto. Certain embodiments of the invention improve the as-sintered density and internal quality of molded articles while reducing the need for costly fine powders and complex injection molds. Articles made by the inventive methods disclosed and claimed herein provide density, and other material properties, similar to those of wrought articles.

In certain embodiments, the inventive subject matter is directed to the use of powder metal processing to create complex preform shapes that are subsequently hot or cold forged or coined to net or near net shape. These preform shapes do not have the shape of the net part they will make. But rather the preform shape is designed to require deformation processing to achieve near net or net shape. Their complex shape allows forging nearer to net shape than traditional forging of simple geometric with lower forging forces and fewer hits. Forging of the preform in turn improves the density, metallurgical microstructure and mechanical properties. As used herein, "complex parts" generally means parts that do not have simple geometric forms such as squares, rectangles, circles, and triangles (or corresponding three-dimensional objects such as boxes, spheres and cones). Rather they have more numerous angles, varying tapers, varying radii. A complex part may have an overall simple geometrical form but may be complex because it has multiple surface features, such as protrusions, indentations, apertures, folds, etc.

The classical MIM molding process may be used for preforms less than 12 mm in thickness using a binder and metal powder system consistent with the alloy and part geometry. The Direct Compression (DC) molding process may be used for relatively large preforms of 12 mm or that are otherwise large parts, as defined herein. In the past direct compression molding of powder metal feedstocks has not been found suitable for forming larger parts because the cost of fine metal powders is high, and the debinding process was too long or otherwise problematic. In the inventive subject, this problem is overcome by, for example, using coarser, lower cost powders and a class of binder system that are more readily removed from the larger section.

FIG. 1 shows a general overview of one process according to the inventive subject matter. In step 100 there is a placing into a mold cavity a first feedstock and a second feedstock or an insert, which maybe made from a second feedstock. The second feedstock may differ in composition and/or material properties. For example, it may be the same composition as the first feedstock but of a coarser grade.

In step 110, the contents of the mold cavity are pressurized, and in some embodiments heated, to produce a unitary green preform having portions corresponding to the first and second feedstocks. In step 120 there is debinding of the preform to produce a brown preform. In step 130, the brown preform is sintered to produce an as-sintered or consolidated preform. In step 140, a mechanical or thermechanical densification process is performed on the consolidated preform to produce a densified net or or near-net form or part. A densified form may be subject to further operations to produce a part with desired shape and dimensions. The part is completed when it achieves its desired shape and dimensions, except for optional finishing operations. Finishing operations, such as polishing or texturing may be applied to the densified part to produce a finished part.

Figure 2:
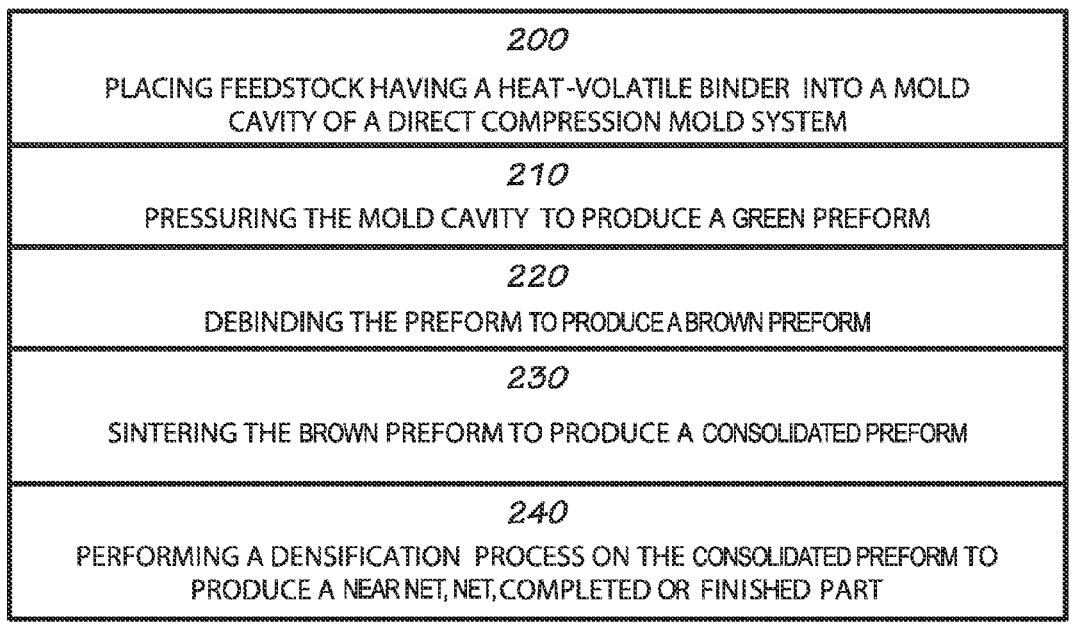
FIG. 2 shows a process map for producing parts from a direct compression method for use in forming large parts.

FIG. 2 shows an overview of another embodiment according to the inventive subject matter. In step 200, feedstock having a heat-volatile binder is placed into a mold cavity of a direct compression mold system. In step 210, the contents of the mold cavity are pressurized to produce a molded green preform. In step 220, there is debinding of the green preform to produce a brown preform. In step 230, the brown preform is sintered to produce an as-sintered or consolidated preform. In step 240, a mechanical or thermechanical densification process is performed on the consolidated preform to produce a densified net or near-net form or part. A densified form may be subject to further operations to produce a part with desired shape and dimensions. The part is completed when it achieves its desired shape and dimensions, except for optional finishing operations. Finishing operations, such as polishing or texturing may be applied to the densified part to produce a finished part.

The systems provide debinding without the need for solvent-based time-consuming solvent extractions or elevated temperature that cause oxidation or other reactions with the metal powders. Such volatile binder systems include water-based materials, such as agar (polysaccharide) or aromatics, such as naphthalene or paradichlorobenzene. In such systems, there are generally two components: (1) a volatizable carrier component that carries the metal or ceramic particles making the feedstock flowable or shapeable; and (2) a backbone component, which remains after volatizing of the carrier component and that makes the metal and/or ceramic particles bind or adhere together. In agar, for example, water may be the carrier and agar is the backbone. A typical agar binder system uses about 80% by weight water. In an acetal binder system, polyethylene gycol, for example, may be the carrier and acetal is backbone. Therefore, the debinding techniques disclosed herein may be defined in terms of two debinding substeps: (1) removal of the carrier with drying, sublimation, dissolving in a solvent, or a catalytic reaction; and (2) low temp heat and/or vacuum (these conditions are relative to sintering conditions) decomposition of backbone solids at more elevated temperatures, which may be provided in a pre-sintering step or during sintering. The volatilization of the carrier leaves micro voids and interstitial spaces between particles or clusters of particles. Transport of the degassed or thermally decomposed backbone solids is facilitated by the micro voids and interstitial paths.

Thus the molding process results in interstitial micro voids which interconnect to form paths for escape of the decomposed backbone binder. The micro voids are in the same size range as the metal or ceramic particles. Micro voids may result not only from the removal of the binders (~same size as the particles) but also from sintering. Post sintering micro voids may be up to 10 times metal or ceramic particle size at low part densities. In contrast, relatively larger and undesirable macro voids can also form as a result of molding defects or from internal pressure generation during debinding. Macro voids can be from 10 times to 100 times the size of the metal or ceramic particles.

A suitable temperature range for volatizing water from a water-based binder system such as an agar system is from room temperature and up. The water volatilizes on a drying interface that advances progressively from the outer surface to the preform interior. The water vapor is transported as a gas through the interconnected interstitial void paths. The agar binder is decomposed from 200 to about 500 degrees F. Aromatic binders, such as naphthalene or paradichlorobenzene, also decompose at low temperatures by subliming on a sublimation interface that advances progressively from the surface to the preform interior. The volatilized aromatic polymer is transported as a gas through the interconnected interstitial void paths. Advantageously, the use of such binders, with their creation of interstitial void paths on an advancing reaction interface, and subsequent gas transport significantly reduces the time of debinding of typical large parts from weeks with conventional solvent systems to hours, making formation of the large parts more feasible. Advantageously, unlike conventional binder systems, those binders disclosed herein generally do not transform at once during primary debinding due to the volatization of the carrier; Rather they have a drying or sublimation interface that progresses from exterior to the interior. This helps ensure that the interstitial paths are interconnected from the inside to the outside to facilitate mass transport of the remaining binder without creating high internal pressures that could create internal bursts or voids.

The DC molding process differs significantly from MIM. The feedstock is not injected under high pressure into a closed mold to create a "packing" pressure in the mold. Rather, a metered amount of flowable feedstock is placed, or injected under low pressure into an open mold. The mold is then closed on the feedstock using the sliding action of an upper ram. The ram continues on its closing stroke until a predetermined "packing" pressure from 500 to 5000 PSI is achieved. The mold is held in the closed position until a critical cooling temperature is met. Alternately, for feedstocks (such as agar) containing a high percent of liquid, the mold pressure can be used to expel some of the liquid from the preform during the "packing" portion of the pressure cycle until a critical dryness condition is met. The mold is then opened and the molded preform ejected. Small preforms are then debound using aqueous, solvent, thermal, or reactive methods depending on the binder, and sintered to achieve densities of 97% or less of theoretical density. Large preforms made with water bearing binders are dried and thermally debound as required, while large preforms made with aromatic binders are thermally debound prior to sintering.

Sintering is performed in a continuous or batch furnace under a protective atmosphere or a vacuum depending on a number of variables including but not limited to binder type and material type.

The described DC molding processes may be used to create a preform suitable for subsequent thermo mechanical processing. The preform does not have the same shape as the finished article. Rather, the preform is designed so that the shape change that occurs during the thermomechanical processing causes an improvement in the resulting density, microstructure and mechanical properties, matching those of annealed wrought materials.

Sintered powder metal preforms may be subjected to a densification process to produce parts that are nearer to net shape, reducing the amount of machining to finish net shape, reducing the machining yield loss and reducing the forging forces required to achieve more complex net shapes. In such densification processes, the mechanical or thermomechanical work provided reduces micro and macro porosity and imparts directionality into the powder process material. The improved density and mechanical properties will match annealed wrought properties. It is believed that forging 10 to 50%, preferably 20% to 40% reduction, at a temperature of about 1600 degrees F. to 2200 degrees F. will achieve a density of 98% or more of the alloy's theoretical density. Subsequent annealing in the material's recrystallization range will refine the grain size.

The inventive subject matter can be used to make complex and relatively large medical parts. For example, as shown in FIGS. 5-12C, the process may be used to form orthopedic components such as acetabular shell, hip stems, tibial trays and articulating parts, shoulder components and spinal plates. It can also be used to make any non-medical products currently made by forging of simple geometric shapes made from wrought material forms. Medical materials include but are not limited to Titanium and its alloys, Cobalt alloys, and Stainless steel alloys.

Figure 5:
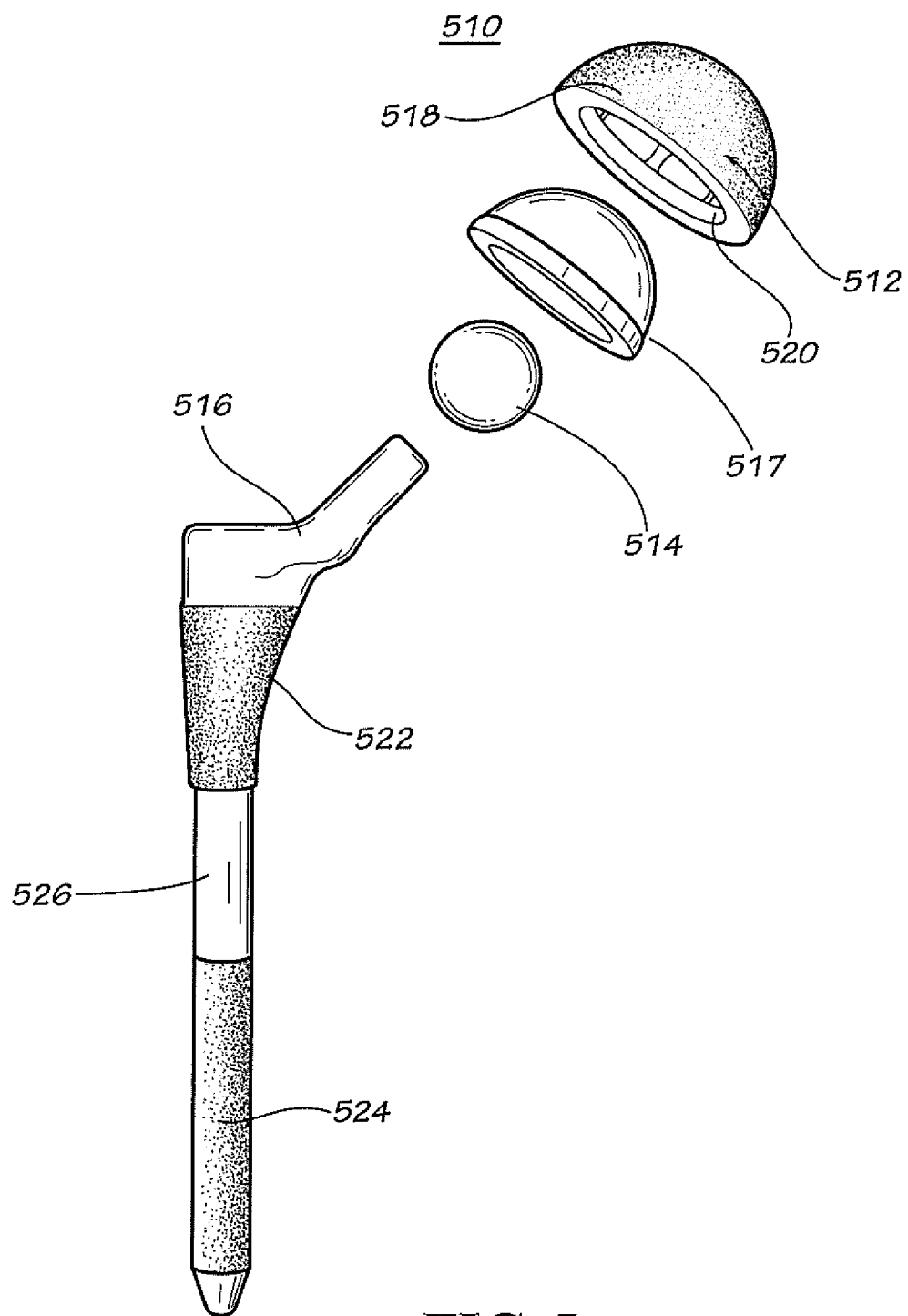
Figure 5A:
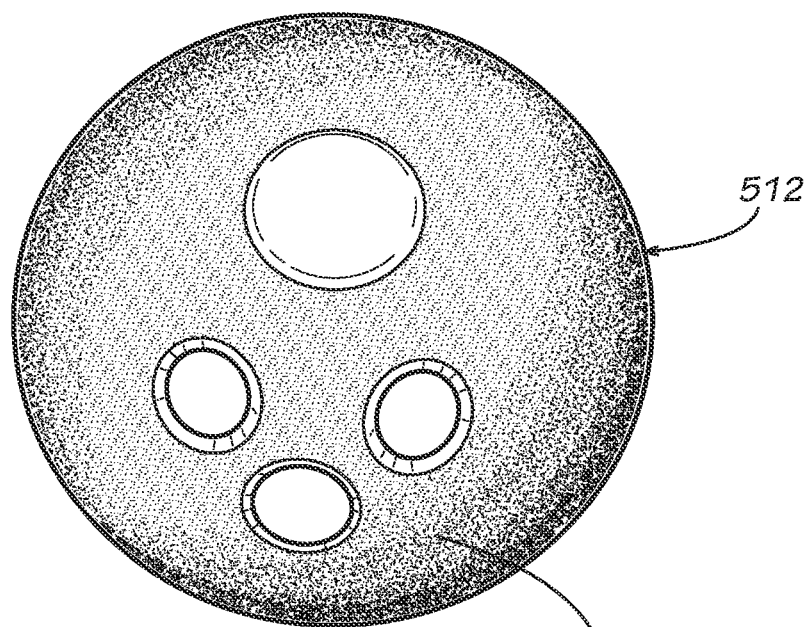
Figure 5B:
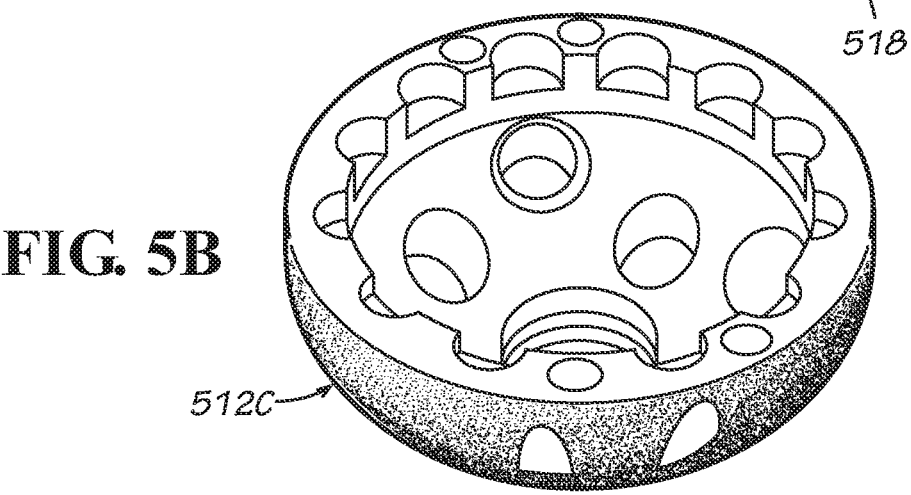
Figure 5C:
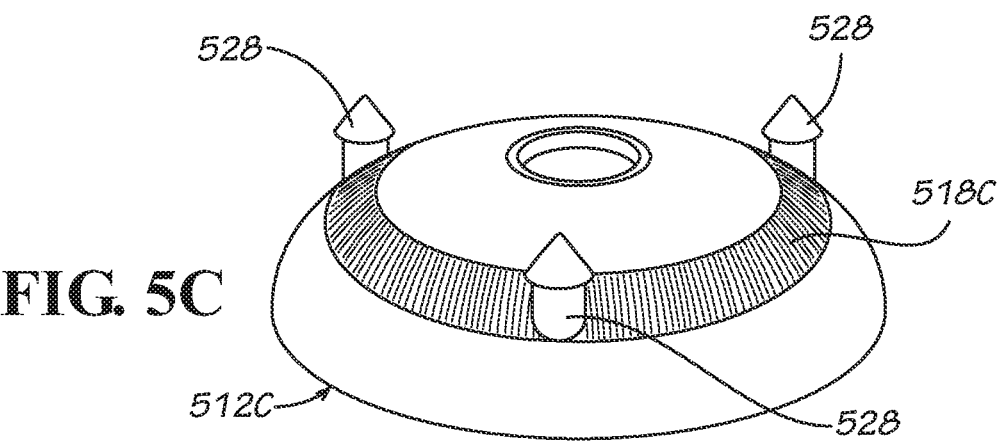

FIG. 5 shows a hip replacement assembly 510 that includes an acetabular shell 512, a femoral head 514, and a femoral stem 516. The assembly also includes a liner 517, which may be a non-metal, such as polyethylene. These parts have bodies that are generally considered large, complex parts. They have angles, varying radii and/or volumetric forms. They may be made according to the inventive PF methods disclosed herein. The parts may be made using the direct compression molding methods and/or they may be made using different powder compositions so that a unitary part has a plurality of different portions. For example, as seen in FIG. 5, the outer surface of the acetabular shell may have smooth sections and/or a patterned, roughened or textured surface 518 to facilitate osteointegration with pelvic bone. FIG. 5A shows the surface 518 in more detail. The surface 518 may be an outer portion of the shell made from a first composition or particle size of powder. The outer portion may surround an inner portion 520 of the shell made from a different composition or particle size of powder. The surface 518 of the outer portion may be formed, for example, by sintering beads of powder onto the inner portion of the shell. Similarly, the femoral stem may have patterned, roughened or textured surfaces 522, 524 for osteointegration with the femur, as well as smooth sections 526. That surface may be an outer portion of the stem that surrounds or overlies an inner portion, the portions differing in composition or particle size. FIG. 5B shows the bottom view of the shell of FIG. 5A. FIG. 5C shows an alternative embodiment of a shell 512C with surfaces patterning 518C and protrusions 528.

Figure 6:
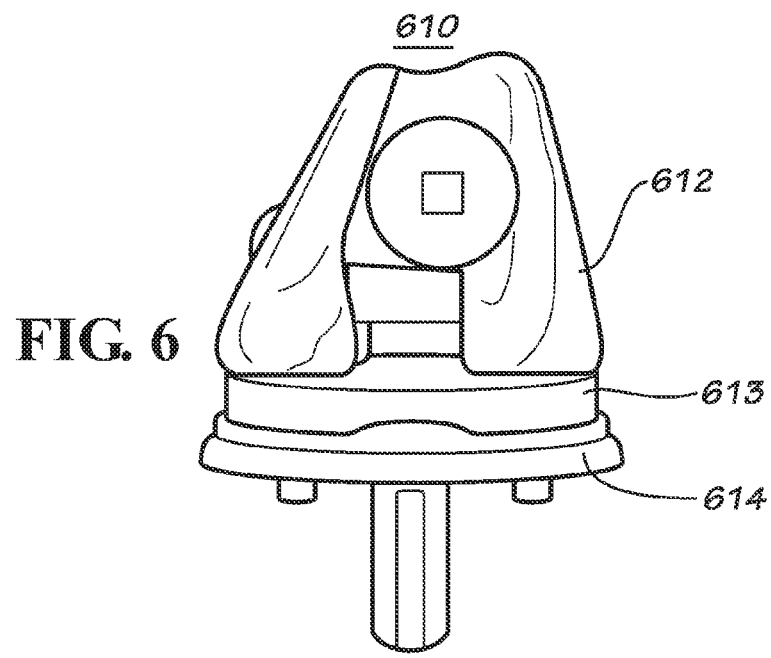
Figures 6A, 6B:
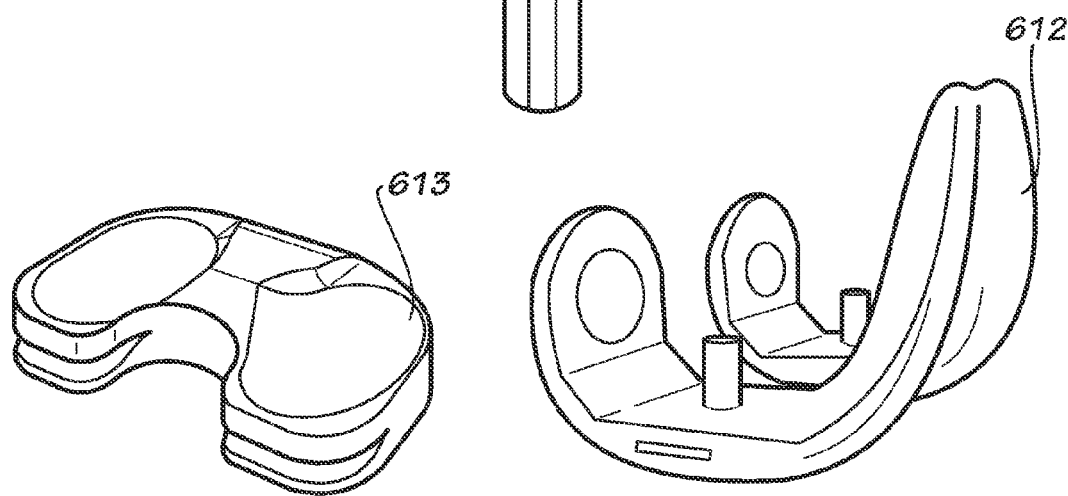
Figure 6C:
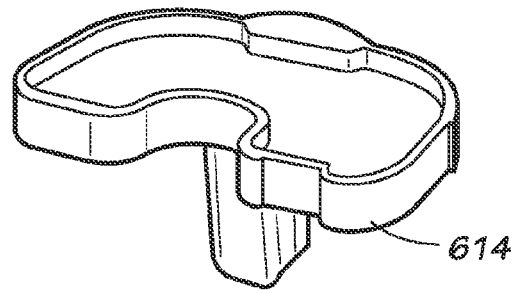

As another example, FIG. 6 shows a knee replacement assembly 610 that includes a femoral component 612 and a tibial tray 614. The assembly also includes a tibial insert 613, which may be a non-metal, such as polyethylene. These parts are generally considered large, complex parts. They may be made according to the inventive PF methods disclosed herein. The parts may be made using the direct compression molding methods and/or they may be made using different powder compositions or particle sizes so that a unitary part has a plurality of different portions. The outer surface of one or both parts may have a smooth, patterned, roughened and/or textured surface, as described above, for example. It may comprise two or more portions made from different powder compositions or particle sizes, as described above, for example.

Figure 7:
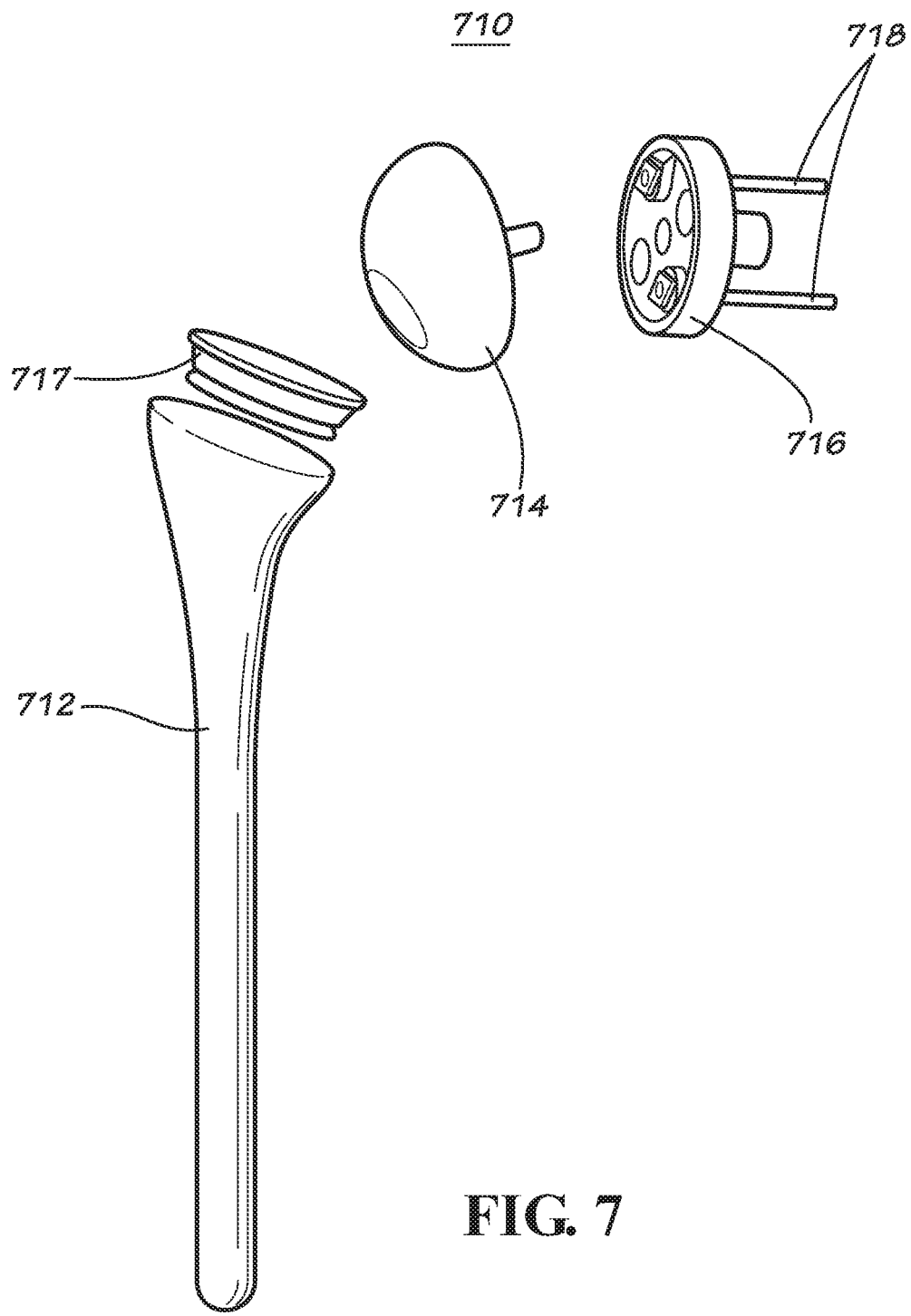

As another example, FIG. 7 shows a shoulder replacement assembly 710 that includes an humeral stem component 712, a glenoid sphere 714, and a glenoid fixation device 716 with a plurality of screws 718. The assembly also includes a spacer 717, which may be a non-metal, such as polyethylene. These parts are generally considered large, complex parts. They may be made according to the inventive PF methods disclosed herein. The parts may be made using the direct compression molding methods and/or they may be made using different powder compositions or particle sizes so that a unitary part has a plurality of different portions. The outer surface of one or both parts may have a smooth, patterned, roughened and/or textured surface, as described above, for example. It may comprise two or more portions made from different powder compositions or particle sizes, as described above, for example.

Figure 8:
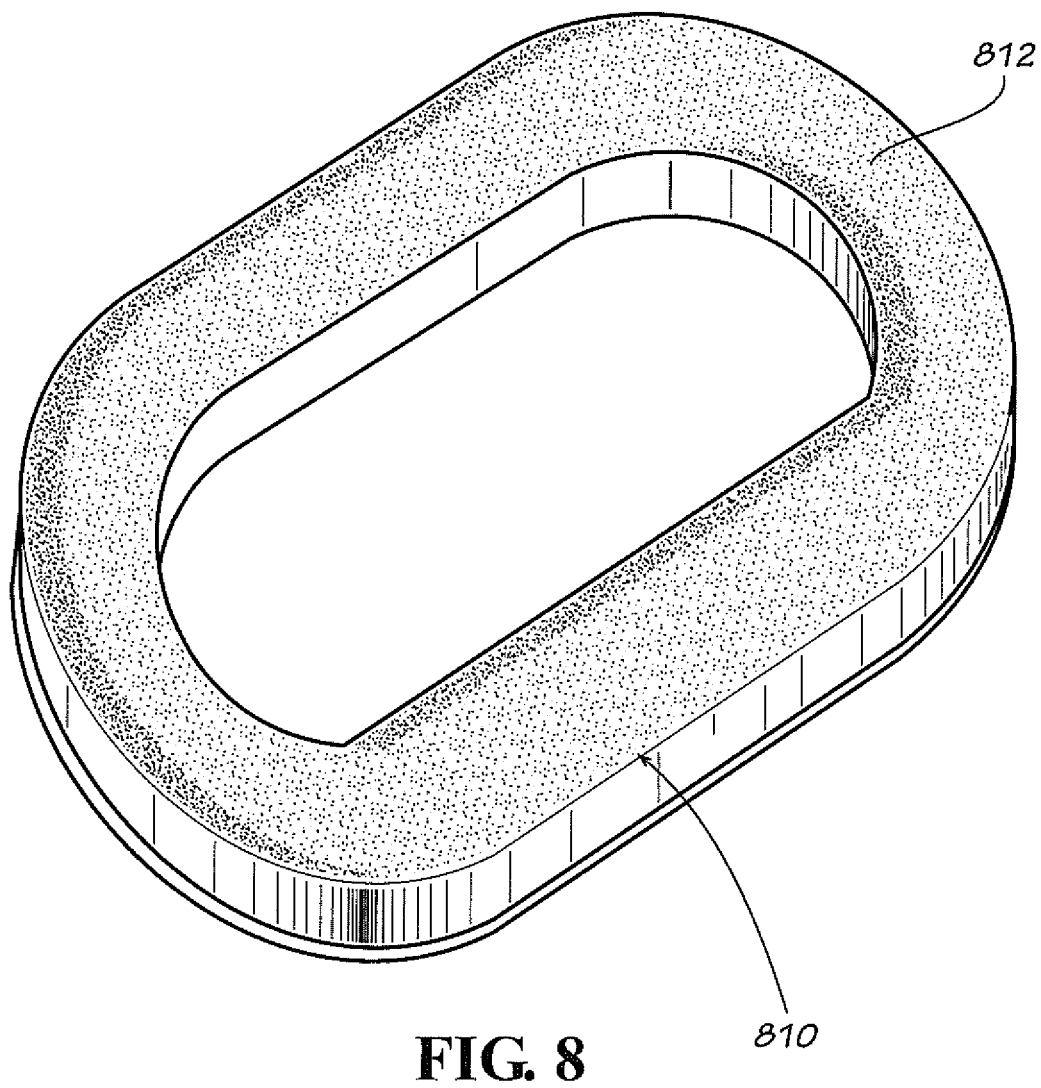

As another example, FIG. 8 shows a lumbar fixation device 810. It is generally considered a large, complex part. It may be made according to the inventive PF methods disclosed herein. The part may be made using the direct compression molding methods and/or it may be made using different powder compositions or particle sizes so that a unitary part has a plurality of different portions. The outer surface may have a smooth, patterned, roughened and/or textured surface, as described above, for example. It may comprise two or more portions made from different powder compositions or powder particle sizes, as described above, for example.

Figure 9:
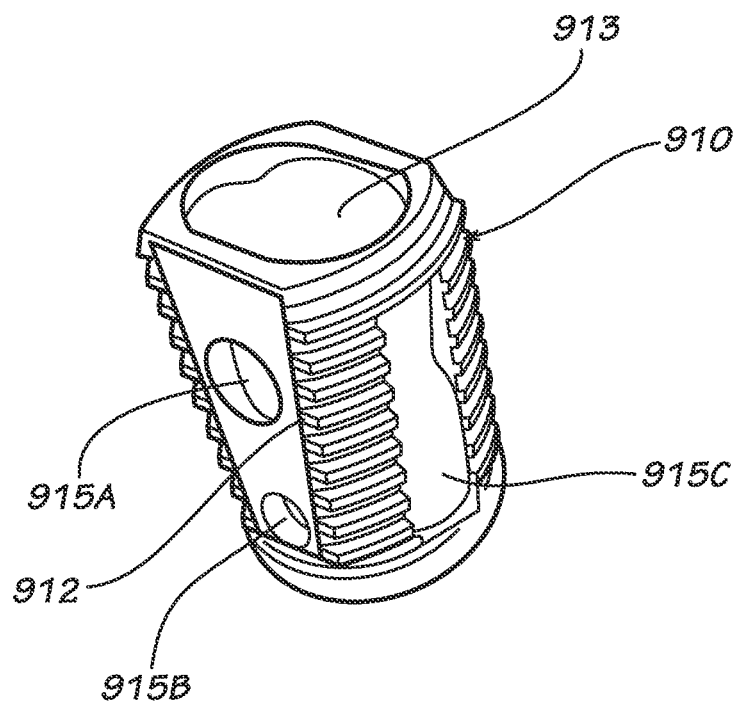
Figure 9A:
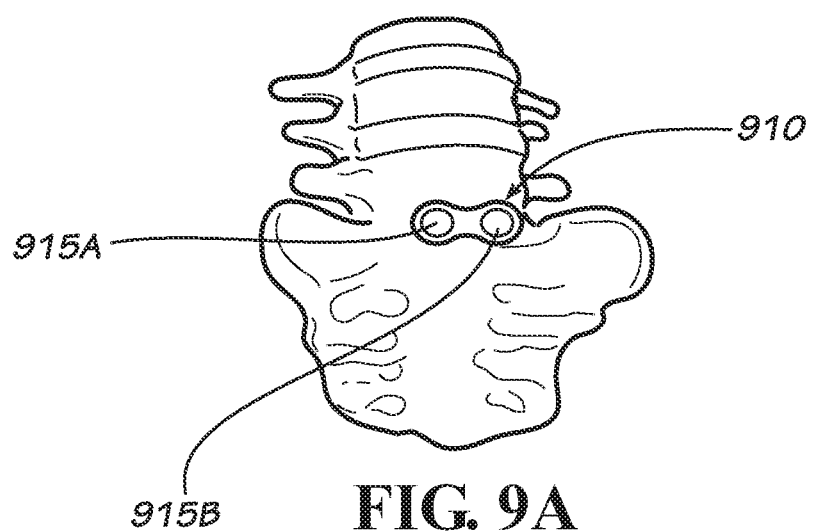

As another example, FIG. 9 shows an orthopedic screw 910 used to couple adjacent vertebrae 1 (FIG. 12C) or other bones in a bone fusion process. The device has a central channel 913 for holding a biopharmaceutical agent that facilitates fusion of the vertebrae. Apertures 915A-C are provided in the device for the release of the agent. The device is generally considered a large, complex part. It may be made according to the inventive PF methods disclosed herein. A pressure forming technique such as extrusion forming may be particularly suitable for forming parts or subparts with long slender profiles. Although not as suitable, the part may be made using the direct compression molding methods and/or it may be made using different powder compositions so that a unitary part has a plurality of different portions. The outer surface may have a smooth, patterned, roughened and/or textured surface, as described above, for example. It may comprise two or more portions made from different powder compositions, as described above, for example.

Figure 10:
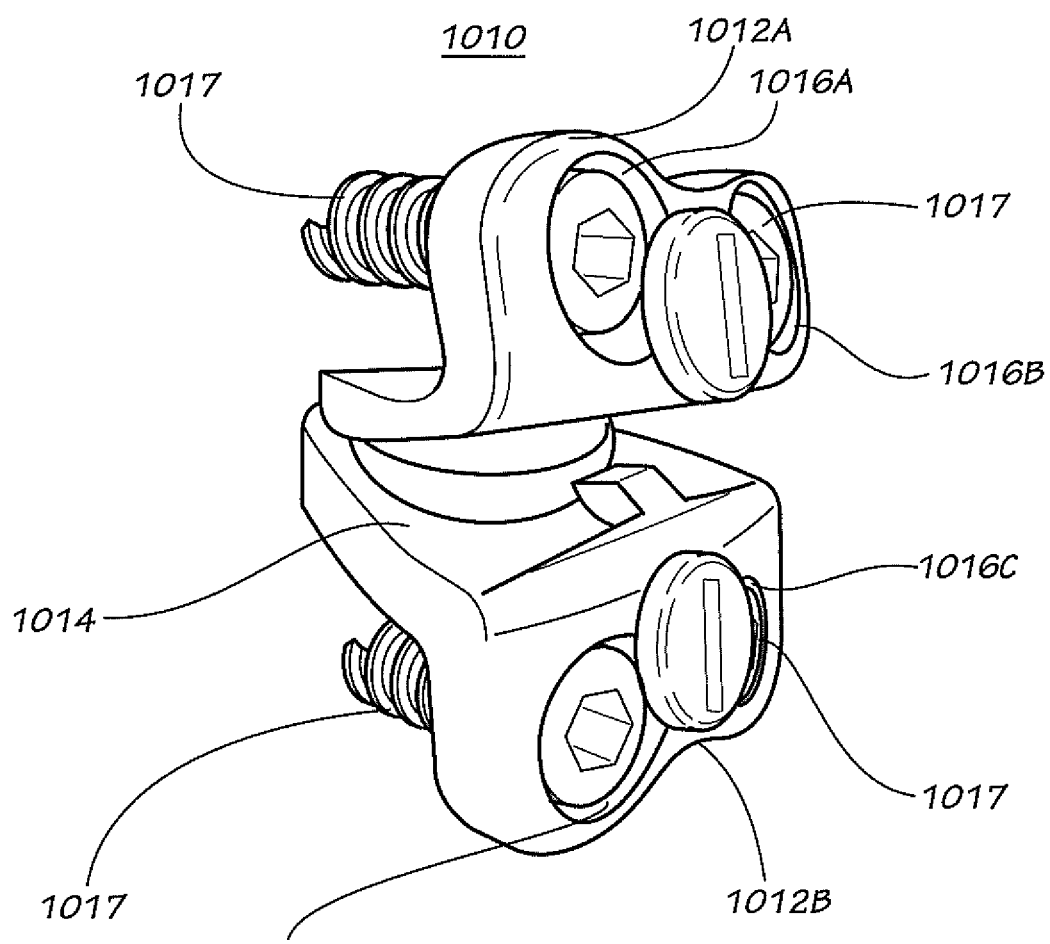

As another example, FIG. 10 shows a disc replacement device 1010 used to couple adjacent vertebrae. The device may be made of a biocompatible Cobalt-Chrome alloy, for example. The device has a generally V-shape that extends between adjacent vertebrae, with transverse portions that couple to the outer surfaces of the adjacent vertebrae. The V may be formed of separate pieces 1012A-B and come together around a pivot 1014 at the apex of the V to allow for some rotation of the adjacent vertebrae. The device provides flexion between the coupled vertebrae. Apertures 1016A-D are provided in the device for the placement of screws 1017 or other such fasteners to anchor the device to the anatomy. The device is generally considered a large, complex part. It may be made according to the inventive PF methods disclosed herein. The part may be made using the direct compression molding methods and/or it may be made using different powder compositions or particle size so that a unitary part has a plurality of different portions. The outer surface may have a smooth, patterned, roughened and/or textured surface, as described above, for example. It may comprise two or more portions made from different powder compositions or particle size, as described above, for example.

Figure 11:
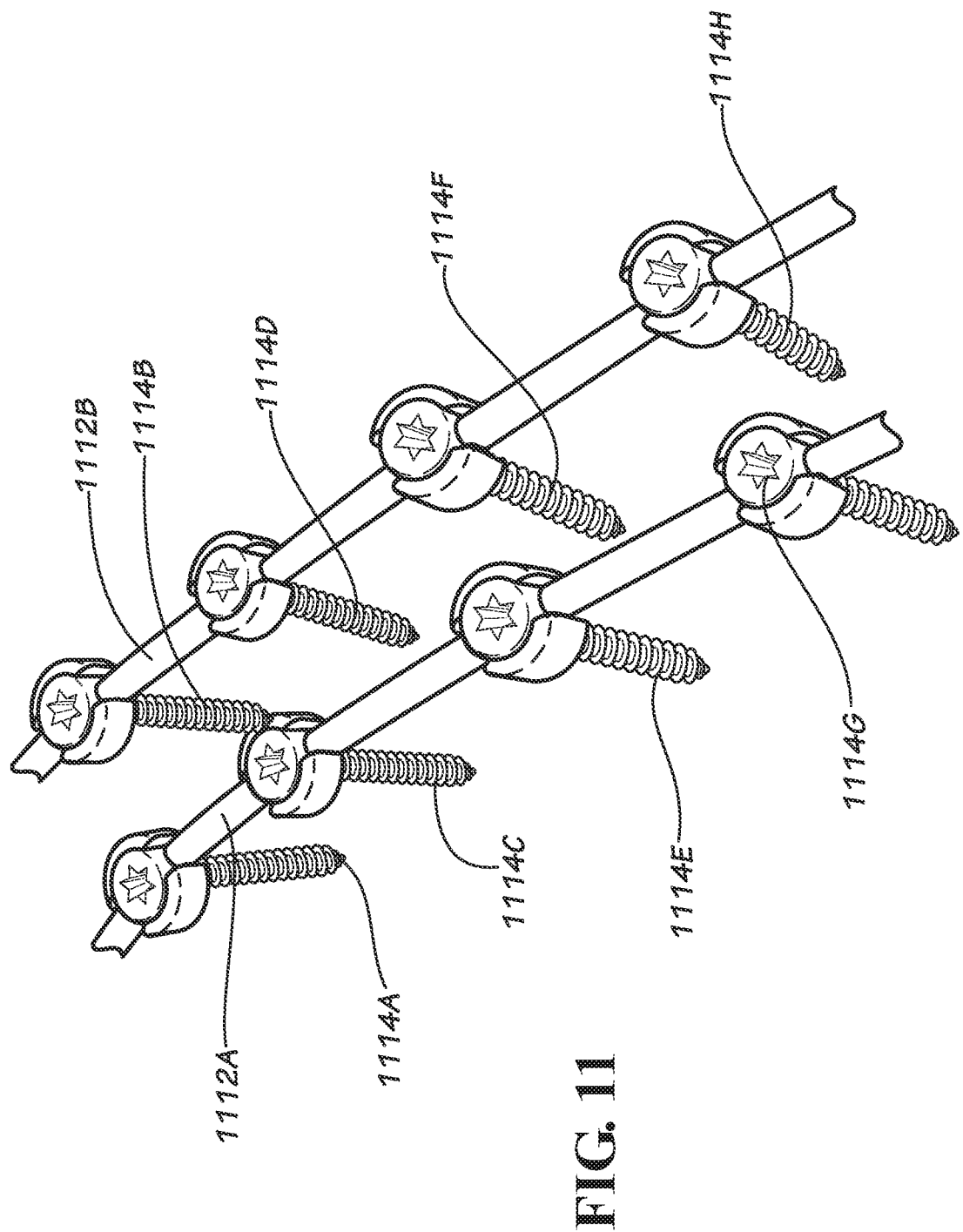

As another example, FIG. 11 shows a spinal fixation assembly 1110 that includes a set of elongate, parallel rods 1112A-B and associated screws 1114E-H that are placed through apertures in the rods and anchor the rods to the spine. The assembly may be made of a Titanium or Titanium alloy, for example. A pressure forming technique such as extrusion forming may be particularly suitable for forming parts or subparts with long slender profiles. Although not as suitable, the parts may be made using the direct compression molding methods and/or they may be made using different powder compositions so that a unitary part has a plurality of different portions. The outer surface of one or both parts may have a smooth, patterned, roughened and/or textured surface, as described above, for example. It may comprise two or more portions made from different powder compositions, as described above, for example.

Figure 12C:
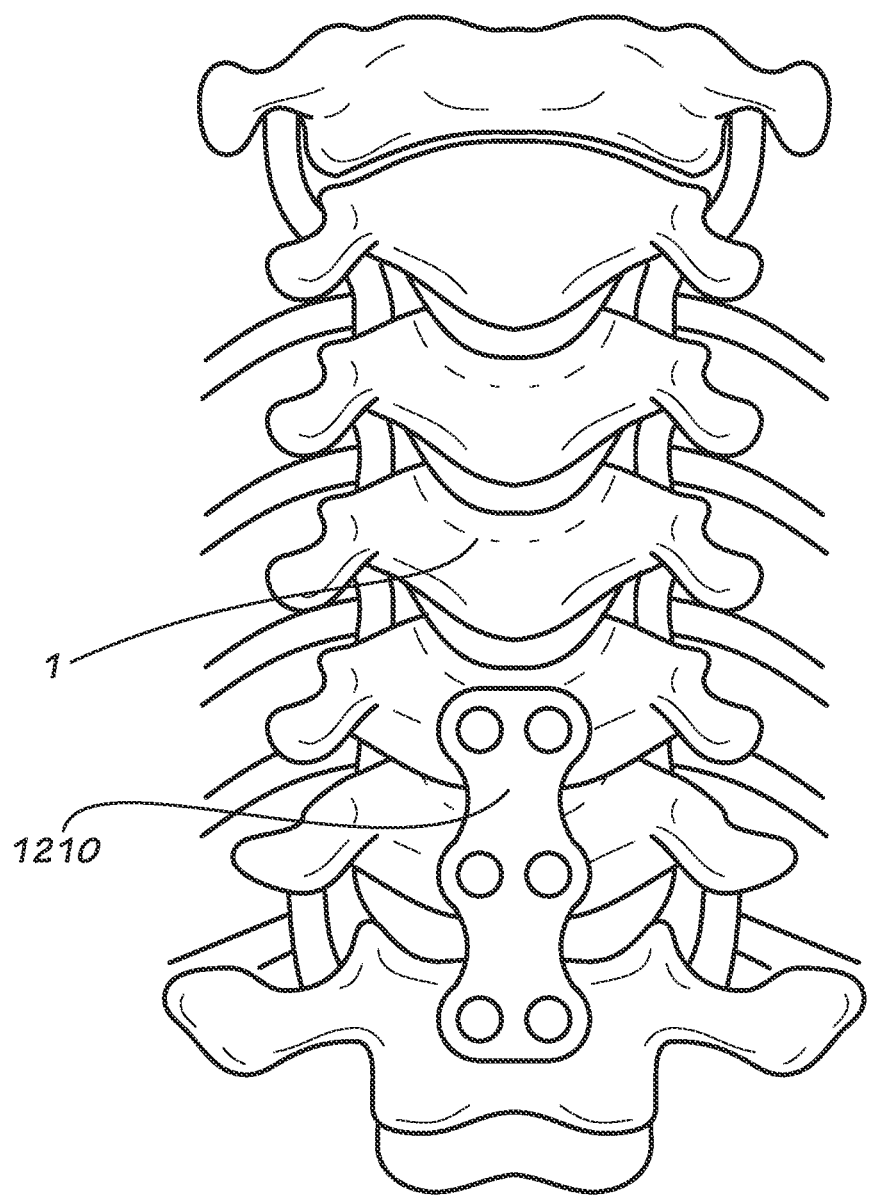

As another example, FIGS. 12A-B shows examples of spinal fixation plates 1210A-B. Each is used to couple two or more adjacent vertebrae in fixed relation. The assembly may be made of a Titanium or Titanium alloy, for example. FIG. 12C shows a plate coupling three vertebrae 1. Apertures 1211A-H are provided in the device for the placement of screws 1212A-H or other such fasteners to anchor the device to the anatomy. The device has a thickness less than 12 mm. It may be made according to the inventive PF methods disclosed herein. The part may be made using the MIM or direct compression molding methods and/or it may be made using different powder compositions so that a unitary part has a plurality of different portions. The outer surface may have a smooth, patterned, roughened and/or textured surface, as described above, for example. It may comprise two or more portions made from different powder compositions or particle sizes, as described above, for example.

In certain embodiments, one or more inserts in the nature of integral cores are provided to a mold for direct compression molding or mold for injection of feedstock (MIM). The core may be in a brown state, i.e. debound state. The inventive subject matter further contemplates that the integral core may be in a green state, i.e., as-molded state not subjected to a debinding operation. The remaining mold cavity space is subsequently filled with a powder and binder feedstock composition. The core may be shaped as, by way of example and without limitation, a sphere, cylindrical disk, pyramid, hexagonal disk, or cube. In still other embodiments, the molding operation may include more than one core in a brown state, green state, or combinations thereof. In still further embodiments, the core is composed of a different composition or particle size than the remainder of the article. As used herein, integral core indicates that the core is a portion of a unitary part. An insert that is a core may be considered a portion that has 50% or more of its surface area surrounded by another portion, in which case the core is "substantially" surrounded.

Figure 3:
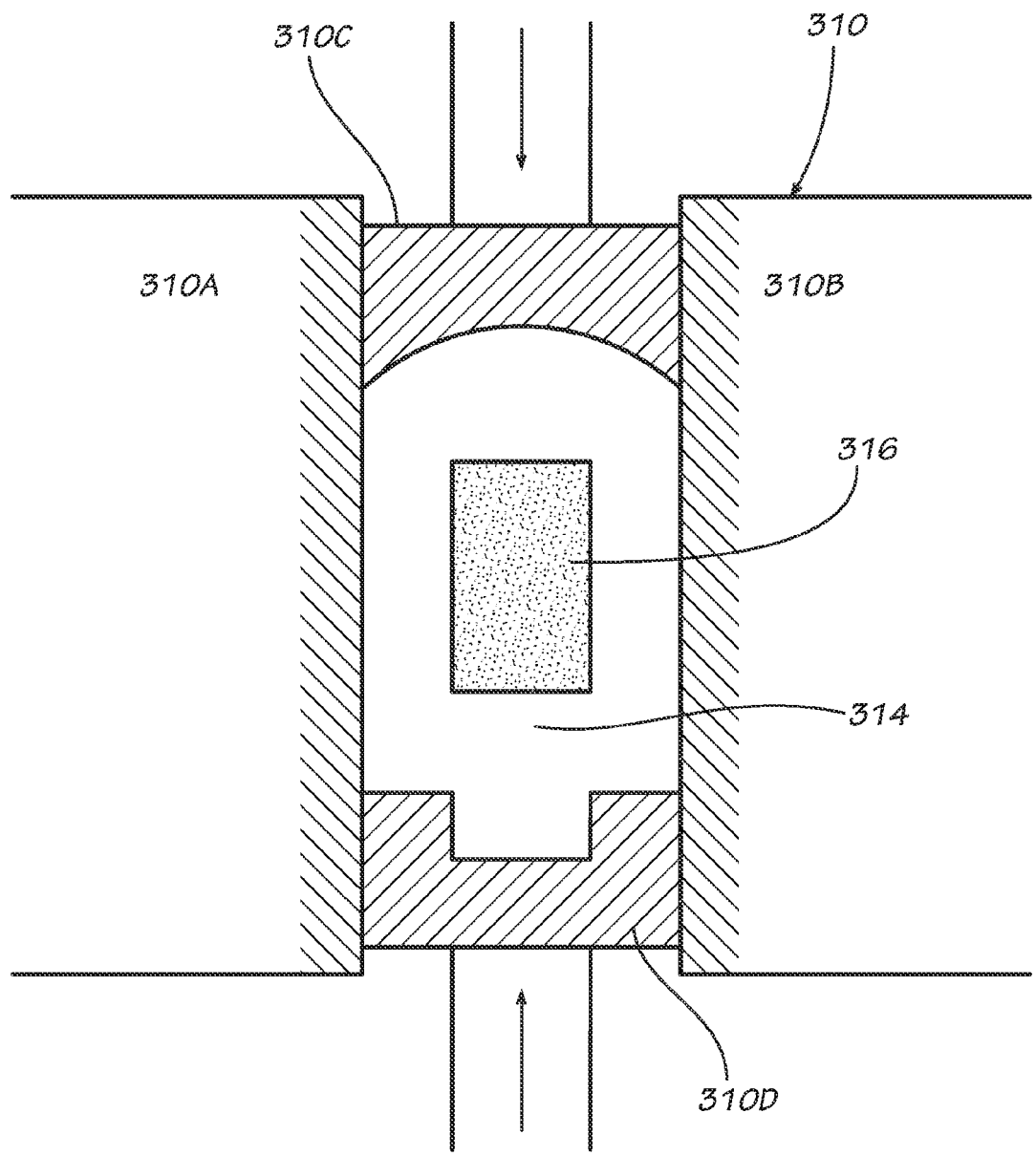
FIG. 3 depicts direct compression molding with a single integral core.
Figure 4:
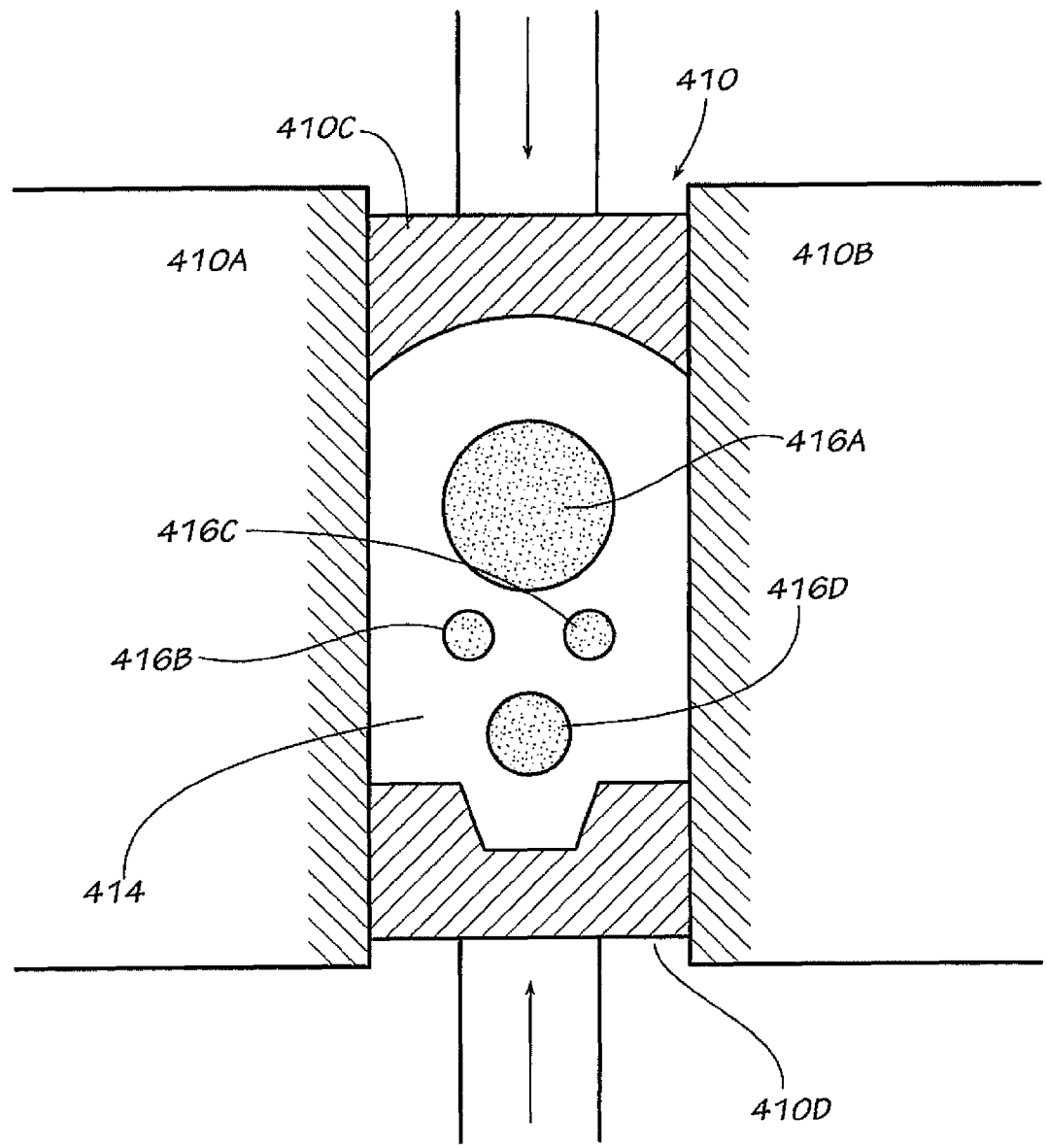
FIG. 4 depicts direct compression molding with multiple integral cores.

FIGS. 3-4 show representative schematic, sectional views of a mold for direct compression of a preform having portions made from different compositions of metal or ceramic powders. In FIG. 3, the mold 310 consists of a cavity 314 defined by fixed walls 310A and 310B. The mold includes movable walls 310C and 310D. The inner surfaces of these walls define the shape of a preform. The arrows indicate the pressure being applied to the movable portions to compress contents in the cavity. The cavity receives feedstock that is pressed into the shape of the preform. A second feedstock or core or formed metal preform or other form or part may be placed into the mold. In this example, an insert in the nature of a green or brown core 316 is placed into the mold and a feedstock that is the same or different composition or particle size fills the cavity space around the core. Pressure is applied to walls 310C and 310D to form a unitary preform with an integral core. FIG. 4 represents a similar mold fixed having walls 410A and 410B and movable walls 410C and 410D, defining cavity 414. In this case, there are a plurality of inserted materials or cores 416A-D which may be based on the same or differing compositions or the same or different particle sizes. Feedstock is filled into the cavity space around these cores and pressure is applied to create a unitary preform of a part.

The composition may comprise at least one metal powder having particles from about 2 microns to about 150 microns, preferably about 25 microns to about 150 microns, in size. The inventive subject matter also contemplates the use of at least one ceramic powder having particles from about 2 microns to about 150 microns, preferably about 25 microns to about 150 microns, in size. These ceramic powders may include alumina, yttria, lanthanum oxide or zirconia particles. The finished article's design requirements and desired material properties will dictate the type and size of powders used.

MIM operations generally avoid use of relatively large particles due to among other things, the development of non-optimal microstructure resulting from several kinetic and thermodynamic factors. For example, large particle arrangement and rearrangement, collapse of pores and micro voids, and fracturing of particle agglomerates all critically effect density and microstructure development during MIM operations. Indeed, articles made from coarse particles are traditionally seen as having excessive internal and/or surface porosity due to slow or incomplete densification. Without being limited by theory, certain embodiments of the inventive subject matter facilitate improved microstructure by performing at least one thermal, mechanical, or combined thermomechanical forming process upon the molded and sintered article. This secondary operation, aids densification by the application of mechanical force and/or heat to reduce internal porosity, surface porosity, or both. Thus, the greater porosity and rougher surface consistent with the use of coarser powders may be at least partially addressed during the later forming process applied to the sintered preform of a part.

For producing articles by the method(s) of the inventive subject matter, the metal powders may be elemental or prealloyed. The metal powders may include, but are not limited to, powders capable of forming alloys suitable for the medical industry, in particular alloys suitable for implantation.

The metal powder compositions for use with the inventive subject matter generally include any powder composition suitable for forming a green preform of a part. Compositions that provide biocompatible metals for use in medical applications are of particular interest. Example compositions include austenitic, stainless steels, including stainless steels per ASTM F138 and ASTM F1314. Titanium, including commercially pure Titanium per ASTM F67, Ti 6Al 4V per ASTM F1472, Ti 6Al 4V ELI per ASTM F136, Ti 6Al 7Nb per ASTM F1295; Nitinol per ASTM F2063; Cobalt alloys, including Cobalt Chromium Molybdenum (CoCrMo) per ASTM F75 or ASTM F1537; Cobalt Chromium Tungsten per ASTM F90; Cobalt Nickel Chromium per ASTM F562; combinations thereof, and other existing and developed alloys designed to have specific properties. (All ASTM standards are according to the standard in effect in year 2010. However, it is recognized that the standards may change with time, and the inventive subject matter is intended to cover updates to the current standards or replacements.

The metal powder may include one or more radiopaque materials that preclude penetration of x-rays or other types of radiation commonly used in diagnostic imaging, which may be particularly advantageous in the medical device field. The metal powders may also include reactive powder metal alloys. Powders suitable for the inventive subject matter may be produced by grinding, milling, spray pyrolysis, liquid atomization, gas atomization, plasma atomization, precipitation, direct reduction of a metal compound, hydride/dehydride, or by other methods.

The metal powder, ceramic powder, or both may be mixed with any number of binders commonly used in metal injection molding. The binders may include at least one polymer that provides sufficient green strength to the composition to maintain a cross-sectional shape after removal from the direct compression mold. The inventive subject matter also contemplates the use of binders that may also include at least one of a lubricant, debinding accelerator, plasticizer, and surfactant. The binder may be, without limitation, acetal, polyethylene, polypropylene, polystyrene, polyethylene glycol, polyalkylene glycol, paraffin wax, oleic acid, polysaccharide (agar), naphthalene, paradichlorobenzene or combinations thereof. A metal powder and binder composition suitable for many applications has about 35% to about 65% by volume of binder. In typical applications, the powder is thoroughly wetted by the binder Feedstock, together with at least one green state or brown state core, are provided to a direct compression molding apparatus and molded to a desired cross-sectional shape. In certain embodiments, at least one core may be made from the same constituent powder of the same particle size and binder composition as the feedstock. Alternately, the core may be made from a different composition or particle size as the feedstock. During the direct compression molding process, thermal and pressure gradients may be controlled to facilitate production of a substantially macro void free product. The molding temperature is preferably less than about 950° F. and is more preferably in the range of about 100° F. to about 650° F., but may range higher. The temperature may be affected by several process factors including, but not limited to, the composition and size of the starting metal powders, the composition of the binders, the volume fraction of metal powder to binder and the number and relative volume of fraction of the integral core(s).

Molding pressure is dependent on process factors including the composition and size of bulk of material powders, the composition of the binders, and ratio of metal powders to binders in the mixture, as well as the number and relative volume fraction of the integral core(s). Typically; the pressure will be from about 500 to about 5000 PSI. The volume fraction of the integral core(s) may range from 5% to 85%, preferably 35 to 75%. The percent will vary with the relative size of the core(s) to the mold cavity, and the desire to keep the overmolded feedstock thickness thin enough for free molding, debinding, and sintering.

The "quality" of the consolidated green state article will have a very strong effect of the properties of the final sintered product. Direct compression molding accordingly facilitates the production of an article having at least near-final shape (at a larger size) while providing excellent dimensional tolerances and surface finish. Still further, certain flaws in the consolidated green state microstructure may be addressed. For example, fine internal or surface porosity may be closed during compression. Stress and velocity gradients have an effect upon composition compaction. These gradients are, in turn, affected by a number of process variables including, but not limited to, the composition and size of the powders, the composition of the binders, the ratio of powders to binders, temperature, pressure, gas solubility, tooling design, the number and/or volume fraction of the integral core(s), and friction. Mitigation of these gradients is especially important during compression in order to minimize undesirable properties such as excessive porosity in the green article.

In this regard, thermal management may be used to control the thermal gradient from the article surface to the article interior during molding operation. In certain embodiments, a powder and binder composition may be provided to a room temperature mold cavity with or without an injection gate, an initial compression force may be applied to the mold, and at least a partial vacuum may be drawn on the mold cavity from the top side. Mold heating may then be applied to the bottom of the mold. Heating may then be applied as a function of the linear distance along the mold surface, i.e. from the bottom of the mold to the top of the mold. In fact, mold heating may be applied to the bottom of the mold to effect at least composition softening, preferably composition melting; mold heating is then moved progressively toward the top of the mold. In this manner, evolved gas, entrapped gas, or both, may be evacuated from the mold cavity. In certain embodiments where composition melting is achieved, mold heating may be advanced so as to progressively move the solid/liquid interface to the top of the mold. Additionally, mold cooling may be applied from the bottom to the top of the mold.

In certain embodiments, mold compression forces may be applied as a function of at least one of applied mold temperature and linear position of the solid/liquid interface. In this manner, for example, an initially low but increasing compression force may be applied during mold heating to better collapse internal and/or surface porosity after at least composition softening is achieved. In yet other embodiments, applied mold temperature may be applied as a function of at least one of mold compression force and position of the solid/liquid interface. In this manner, for example, the rate of mold cooling may increase as the solid/liquid interface approaches the top of the mold After molding, the green state article may be subjected to at least one debinding operation. Debinding may be performed by solvent extraction, super critical fluid extraction, aqueous extraction, chemical decomposition, catalytic decomposition, drying, sublimation or thermal decomposition at one or more elevated temperatures, to produce a "brown" article. Debinding time is affected by a number of process variables including, but not limited to, the binder system, the size and shape of the article, the amount and interconnectivity of internal porosity, the presence or absence of debinding accelerators and the number and relative volume fraction of the core(s). In certain embodiments, debinding is performed under a reduced atmosphere. For example, the shaped article can be heated to about 750° F. for about 3 hours at $1 \times 10^{-3}$ Torr to effect at least partial binder removal. The operation may also include solvent debinding whereby a liquid, supercritical fluid, or gas is used to dissolve the binder.

After debinding, the brown preform may be sintered to effect consolidation. Complete densification is desirable. Consolidation at least 90% of theoretical density is generally achieved for some applications while consolidation to at least 97% of theoretical may be desired for other applications, the degree of consolidation being selected by a person skilled in the art depending on the desired application. The degree of consolidation is determined by measuring the density of the actual part and dividing this by the theoretical density of the part alloy. When expressed as a percent, this defines the part density as a percent of theoretical. MIM parts typically range from 92 to 97% of theoretical density in the as-sintered condition. In comparison, hot isostatically pressed parts and forged parts will exceed 98% of theoretical density. Thus, MIM alone does not achieve sufficient densities and other conventional techniques that do, as discussed in the Background section, are not suitable for forming large or complex parts.

Sintering time to effect a desired consolidation will depend on a variety of factors, including but not limited to, the composition and size of the powder, sintering temperature, the presence or absence of mechanical pressure and initial porosity of the article. The porosity of the sintered body is preferably less than 10%, and more preferably less than 3%. Reduction in porosity contributes to a higher density of the sintered body, yields a high strength and high dimensional precision, reduces sintering defects, and yields a satisfactory appearance. The sintering temperature should be maintained for an appropriate time to allow for diffusion and mass transport effects and to provide for suitable consolidation. In certain embodiments, sintering is performed in a controlled atmosphere that may include, without limitation, hydrogen, argon, nitrogen, vacuum or some combination of these atmospheres. During sintering, shrinkage of the article may occur as the inter-particle pore size is reduced. As such, the article may shrink as much as 20% during the sintering operation to net or near net size. Shrinkage, thus, should be taken into account for mold design, mold selection, and part design.

A mechanical or thermomechanical forming step may include at least one of hot isostatic pressing, cold isostatic pressing, uniaxial compression, biaxial compression, stamping, coining, forging, drawing, rolling, piercing, extrusion, upsetting, swaging, preheating, annealing or combinations thereof. These forming operations will tend to close any remaining micro voids, and reduce the size of macro voids through the effects of the forming operation.

The part that results from sintering and any further densification process may be subject to a finishing operation. The finishing operation may consist of any number of methods, such as coining, coating, deburring, cleaning, polishing, tumbling, or combinations thereof. In this manner, desired tolerances or aesthetic aspects of the article may be finalized to allow for vending, display, or use/functionality.

Various embodiments of the inventive subject matter provide several benefits over conventional metal injection molding (MIM) operations. For example, conventional MIM operations are optimized for batch manufacturing of small parts that have complex geometries and are produced in large quantities. In conventional MIM processes, however, mold filling and subsequent internal macro void formation become problematic at larger article sizes. Use of an integrated core minimizes the tendency for internal macro void formation for large direct compression molded parts. Still further, the green core, or a brown core, reduces the overall debinding time for the fabricated article, and minimizes the risk of internal blister formation due to incomplete debinding. Thermomechanical forming of sintered parts to produce a wrought part will further reduce voids, and increase density. Articles made by the inventive methods disclosed, and claimed herein, provide various benefits including physical properties comparable to those of wrought articles.

COMPARATIVE EXAMPLES

To assess the suitability of certain embodiment of the inventive subject matter, samples of a cobalt, chrome, molybdenum alloy were prepared for comparative analysis. The following tables and referenced figures relate to a metal feedstock composition that was formed into samples that were (1) wrought; (2) as-sintered; (3) sintered and forged; and (4) sintered, forged and annealed powder metal samples and representative microstructures, densities and hardness. The metal composition met the requirements of ASTM F75 and ASTM F1537 Alloy 2 (high carbon). The particle sizes used in the feedstock were from about 15 to about 25 micrometers. The binder system that was used was 5 to 10% weight percent polyethylene glycol and acetal. Mold peak pressure was 1,200 to 2,500 PSI and mold peak temperature was 250 to 400 F. The mold cavity was designed to produce a disk shaped preform 2.15 inch in diameter and 1.25 inch thick. The debinding entailed soaking in a hot water bath at 60 to 85 C for a sufficient time to remove a majority of the carrier binder. The peak sintering temperature was 1250 to 1315 C in a continuous sintering furnace using a reducing atmosphere.

| Hardness Data | | | | | | |
|---|---|---|---|---|---|---|
| | Reading 1 | Reading 2 | Reading 3 | Reading 4 | Reading 5 | Average |
| DC Molded: As-Sintered | | | | | | |
| Near Edge | 28.3 | 29.1 | 29.0 | 29.2 | 27.8 | 28.7 |
| Near Center | 28.1 | 25.6 | 27.2 | 30.1 | 28.4 | 27.9 |
| DC Molded: As-forged 15% reduction | | | | | | |
| Near Edge | 41.5 | 45.0 | 42.1 | 41.7 | 38.0 | 41.7 |
| Near Center | 40.7 | 40.1 | 41.1 | 38.9 | 37.7 | 39.7 |
| DC Molded: As-forged 30% reduction | | | | | | |
| Near Edge | 45.2 | 46.3 | 46.9 | 47.2 | 48.6 | 46.8 |
| Near Center | 43.1 | 43.5 | 41.5 | 45.3 | 45.9 | 43.9 |
| Cross section | Top 45.7 | Middle 42.8 | Bottom 43.3 | | | |
| DC Molded: Forged 15% reduction and annealed | | | | | | |
| Near Edge | 43.5 | 45.0 | 44.1 | 43.1 | 44.0 | 43.9 |
| Near Center | 42.6 | 42.5 | 44.1 | 42.3 | 42.2 | 42.7 |
| DC Molded: Forged 30% reduction and annealed | | | | | | |
| Near Edge | 41.7 | 44.3 | 40.2 | 42.9 | 41.7 | 42.2 |
| Near Center | 38.1 | 41.2 | 39.1 | 41.0 | 36.5 | 39.2 |
| Cross section | Top 43.7 | Middle 43.9 | Bottom 42.8 | | | |
| Wrought: As-forged 15% reduction | | | | | | |
| Near Edge | 49.2 | 49.9 | 50.8 | 49.4 | 49.0 | 49.7 |
| Near Center | 44.2 | 44.1 | 43.8 | 43.0 | 45.7 | 44.2 |
| Wrought: Forged 15% reduction and annealed | | | | | | |
| Near Edge | 44.7 | 44.7 | 45.9 | 44.6 | 44.4 | 44.9 |
| Near Center | 44.5 | 44.6 | 45.6 | 44.7 | 44.8 | 44.8 |
| Wrought: As-forged ~30% reduction | | | | | | |
| Near Edge | 50.6 | 49.6 | 49.6 | 50.6 | 48.7 | 49.8 |
| Near Center | 53.2 | 53.8 | 50.8 | 51.6 | 52.9 | 52.5 |
| Wrought: Forged 30% reduction and annealed | | | | | | |
| Near Edge | 44.2 | 43.9 | 44.4 | 46 | 45.1 | 44.7 |
| Near Center | 45.9 | 45.9 | 45.6 | 45.5 | 45.7 | 45.7 |
| Cross section | Top 44.6 | Middle 44 | Bottom 43.6 | | | |

| Average Hardness (HRC) | | | |
|---|---|---|---|
| | Near Edge | Near Center | Avg |
| 15% Upset Forged | | | |
| MIM As-sintered | 28.7 | 27.9 | 28.3 |
| MIM Forged | 41.7 | 39.7 | 40.7 |
| MIM Forged + Annealed | 43.9 | 42.7 | 43.3 |
| Wrought Forged | 49.7 | 44.2 | 46.95 |
| Wrought Forged + Annealed | 44.9 | 44.8 | 44.85 |
| 30% Upset Forged | | | |
| DC Molded As-sintered | 28.7 | 27.9 | 28.3 |
| DC Molded Forged | 46.8 | 43.9 | 45.35 |
| DC Molded Forged + Annealed | 42.2 | 39.2 | 40.7 |
| Wrought Forged | 49.8 | 52.5 | 51.15 |
| Wrought Forged + Annealed | 44.7 | 45.7 | 45.2 |

| Average Hardness (HRC) | | |
|---|---|---|
| | Near Edge | Near Center |
| DC Molded As-sintered | 28.7 | 27.9 |
| DC Molded Forged 15% | 41.7 | 39.7 |
| DC Molded Forged 15% annealed | 43.9 | 42.7 |
| DC Molded Forged 30% | 46.8 | 43.9 |
| DC Molded Forged 30% annealed | 42.2 | 39.2 |
| Wrought Forged 15% | 49.7 | 44.2 |
| Wrought Forged 15% annealed | 44.9 | 44.8 |

| Theoretical density Measured on Wrought Material |
|---|
| 8.29 g/cm3 |

| Measured Density - Archimedes Method | | |
|---|---|---|
| | g/cm3 | % of theoretical |
| 15% Upset Forged | | |
| DC As-sintered | 7.72 | 93.1% |
| DC Forged | 8.12 | 97.9% |
| DC Forged + Annealed | 8.22 | 99.2% |
| Wrought | 8.29 | 100.0% |

-continued

| Hardness Data | | |
|---|---|---|
| 30% Upset Forged | | |
| DC Molded As-sintered | 7.72 | 93.1% |
| DC Molded Forged | 8.27 | 99.8% |
| DC Molded Forged + Annealed | 8.26 | 99.6% |
| Wrought | 8.29 | 100.0% |

Figure 13:
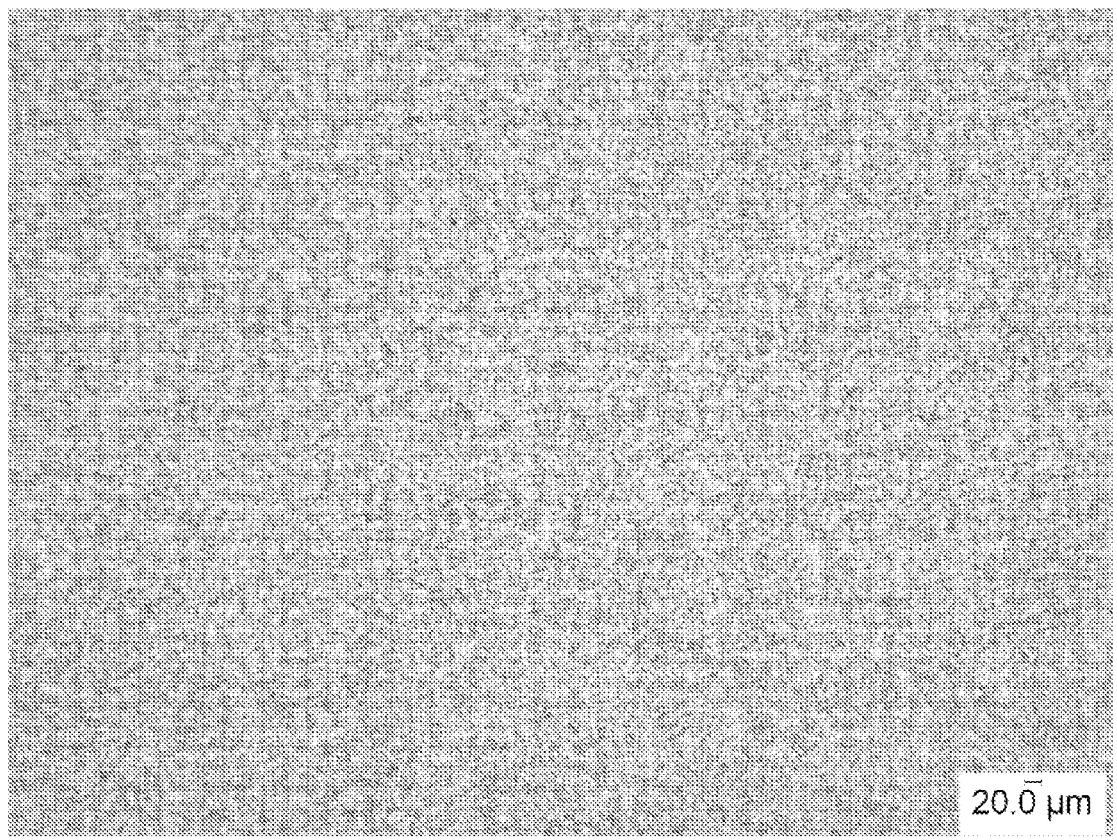
FIG. 13 shows a micrograph of a wrought metal microstructure for comparison with microstructures according to the inventive subject matter.

The following figures are representative micrographs for certain samples formed per the above tables. FIG. 13 shows the microstructure of a wrought, annealed and forged reference metal of the same composition as the sample metals. This reference sample has density and hardness equal to or essentially equal to the theoretical value for F1537 alloy 2 chemistry.

Figure 14:
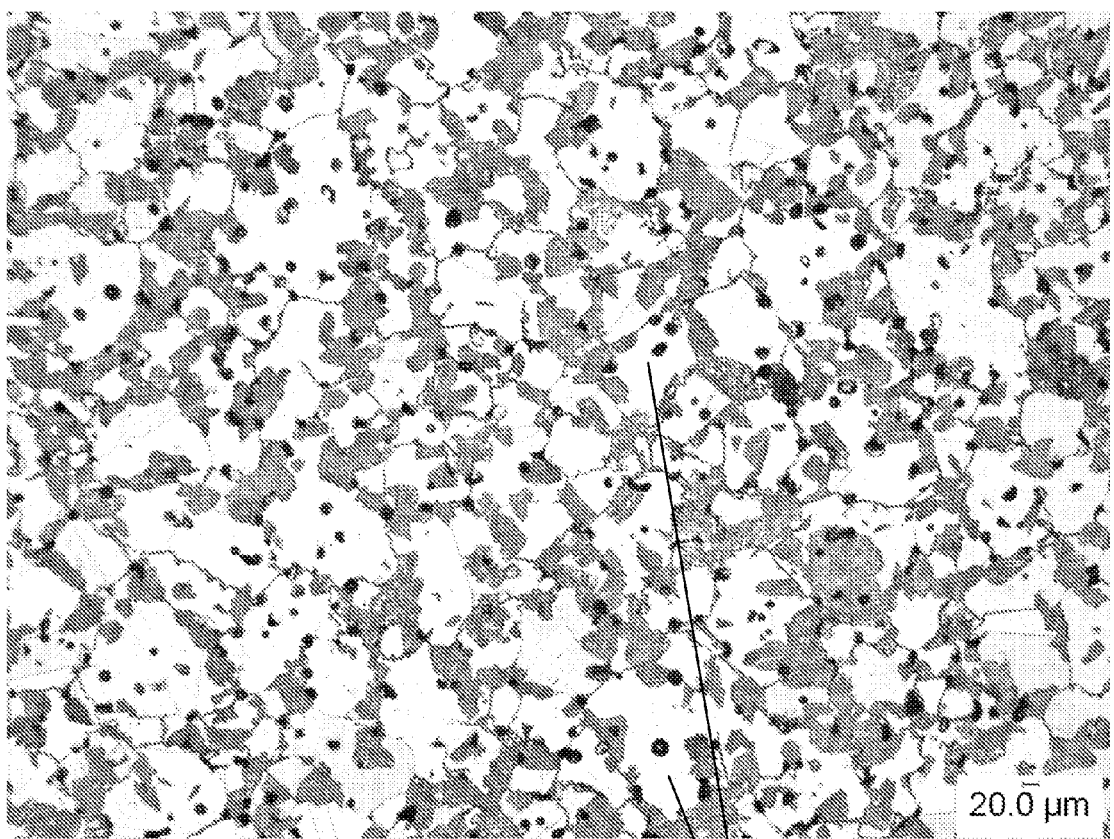
FIG. 14 shows a micrograph of a metal microstructure formed using a direct compression method according to the inventive subject matter.

FIG. 14 shows the microstructure of the as-sintered sample, with no post-sintering processing. The sample had a density of 93.1% of the theoretical density of the alloy The interstitial micro-voids (white areas 1410) can readily be seen, in comparison to the void free microstructure of a wrought metal, which represents 100% theoretical density meeting the standards of ASTM F75 and F1537 Alloy 2.

Figure 15:
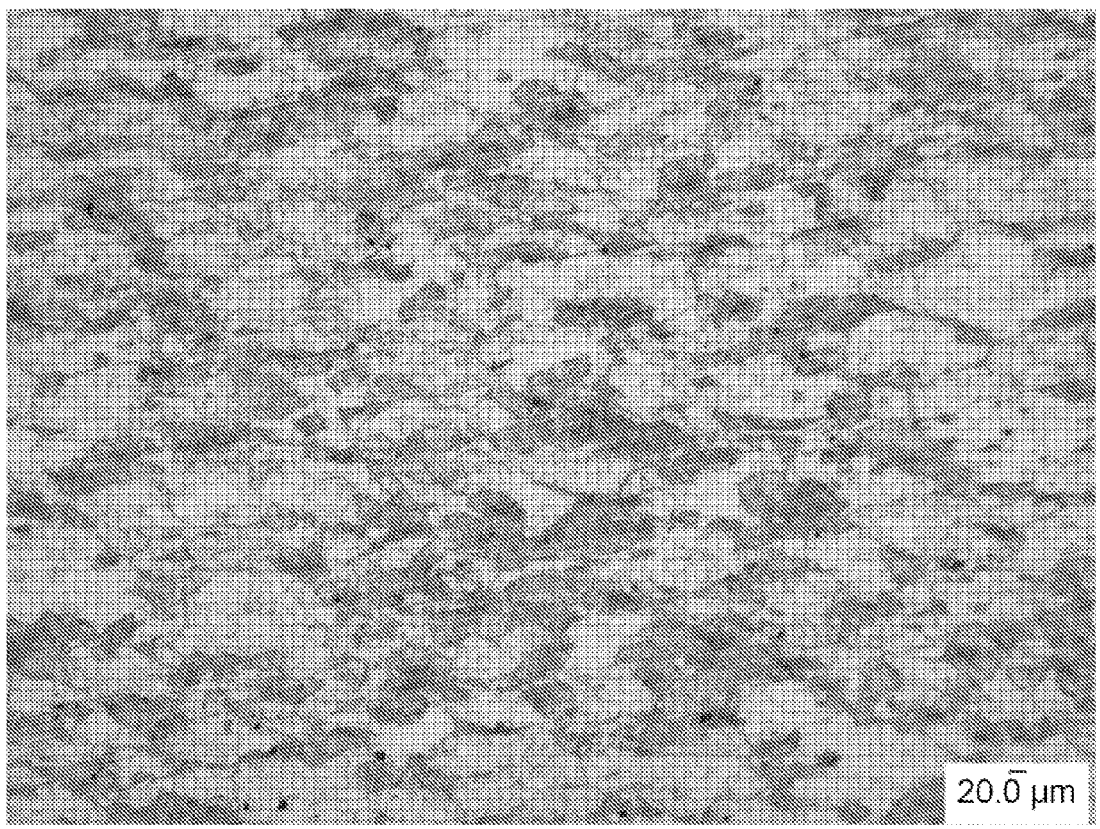
FIG. 15 shows a micrograph of a metal microstructure formed using a thermo mechanical densification process on a metal structure like that in FIG. 14, according to the inventive subject matter.
Figure 16:
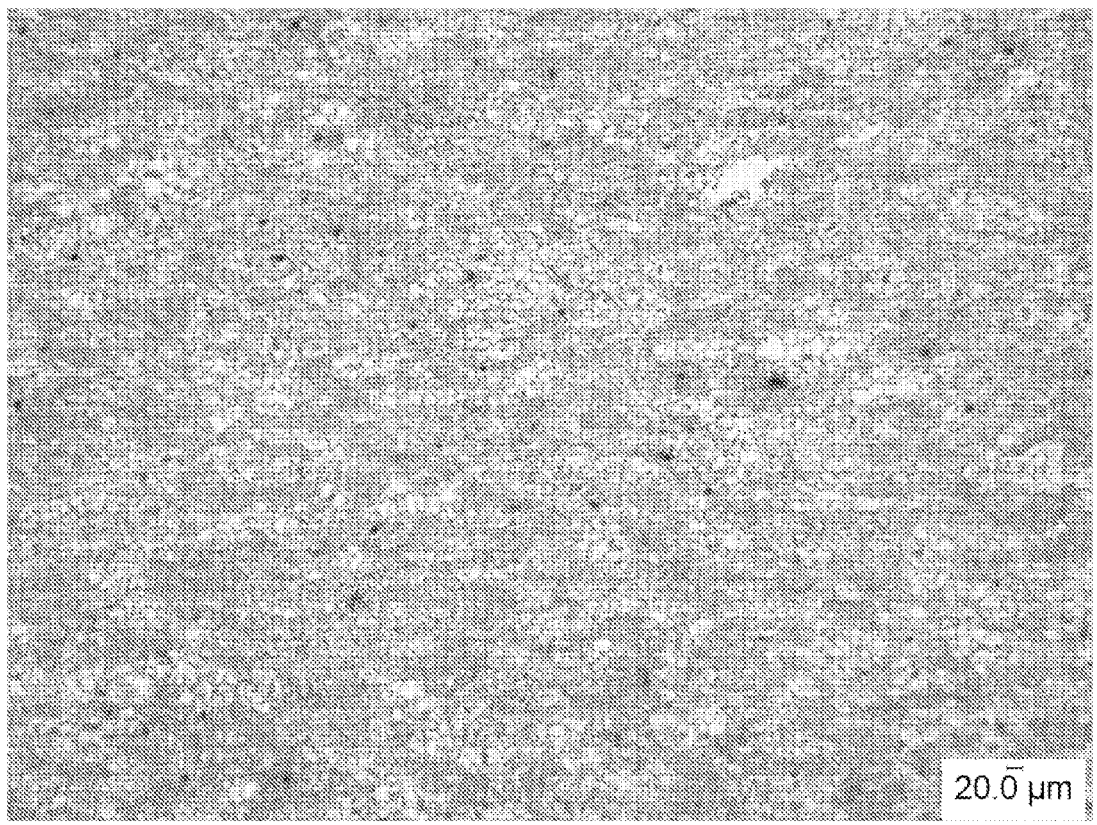
FIG. 16 shows a micrograph of a metal microstructure formed using a further thermal process on a metal structure like that in FIG. 15, according to the inventive subject matter.

FIG. 15 shows a microstructure of a direct compression molded sample made according to the general parameters set forth for the sample of FIG. 13. In this case the sample was forged to a 30% reduction in height. The closing and minimizing of the interstitial micro-voids is evident. FIG. 16 shows a sample like that in FIG. 14 but after an annealing step, demonstrating refinement of the microstructure approximating that of the wrought material shown in FIG. 13.

In illustration of some example applications, on larger preforms, the DC mold could be loaded with coarse powders in the center of the preform and more costly fine powders at the surface. The low cost, coarse powders could be in the form of a green state or preferably brown state core with a simple geometric shape. This shape could be made by extruding and cutting green feedstock or pressing a metered slug of green feedstock in a simple heated mold.

In another possible embodiment, a core(s) made of low cost alloys, large diameter particles or intentionally porous structures could be placed in the center of the part.

Additional advantages and novel features of the certain embodiments of the inventive subject matter will be set forth in part in the description, examples and figures which follow, all of which are intended to be for illustrative purposes only, and not intended in any way to limit the invention, and in part will become apparent to those skilled in the art on examination of the following, or may be learned by practice of the invention.

Persons skilled in the art will recognize that many modifications and variations are possible in the details, materials, and arrangements of the parts and actions which have been described and illustrated in order to explain the nature of the inventive subject matter, and that such modifications and variations do not depart from the spirit and scope of the teachings and claims contained therein.

All patent and non-patent literature cited herein is hereby incorporated by references in its entirety for all purposes.

The invention claimed is:

1. A brown metal, a brown ceramic, or a brown metal and ceramic preform, the preform comprising:
    a) at least one insert, the insert comprising an insert metal powder, an insert ceramic powder, or an insert metal and ceramic powder mixture; and
    b) a first composition surrounding the at least one insert, the first composition comprising:
        i) a first composition metal powder, a first composition ceramic powder, or a combination of the first composition metal and ceramic powders; and
        ii) a binder comprising a carrier component,
    c) wherein at least the first composition has a microstructure that includes micro voids and interstitial paths, the interstitial paths residing between and connecting to adjacent micro voids, and
    d) wherein the micro voids of the first composition have a micro void size that is about 1-10 times a particle size of the first composition metal powder, the first composition ceramic powder, or the combination of the first composition metal and ceramic powders.

2. The preform of claim 1 configured for use as or in a medical device.

3. The preform of claim 1 wherein, after sintering and then forging, at least the first composition has a density that is at least 98% of the first composition's theoretical density prior to being sintered.

4. The preform of claim 1 wherein the insert is relatively less dense than the surrounding first composition.

5. The preform of claim 1 wherein at least the first composition comprises a biocompatible first composition metal selected from the group consisting of a cobalt alloy, titanium, a titanium alloy, and a stainless steel alloy.

6. The preform of claim 1 having a length greater than 4 inches along any dimension.

7. The preform of claim 1 being of a size sufficient to contain a 12 mm diameter sphere.

8. The preform of claim 1 having a thickness greater than 12 mm.

9. The preform of claim 1 wherein the at least one insert is a green state insert.

10. The preform of claim 1 wherein the at least one insert is a brown state insert.

11. The preform of claim 1 wherein the at least one insert is both a green state and a brown state insert.

12. The preform of claim 1 wherein the first composition comprises at least one first composition metal powder having particles from about 2 microns to about 150 microns in size.

13. The preform of claim 12 wherein the at least one first composition metal powder has particles from about 25 microns to about 150 microns in size.

14. The preform of claim 1 wherein the first composition metal powder is selected from the group consisting of: a cobalt alloy, a titanium or titanium alloy and a stainless steel.

15. The preform of claim 1 wherein the first composition comprises a blend of at least one first composition metal powder and at least one first composition ceramic powder.

16. The preform of claim 15 wherein the at least one first composition ceramic powder is from about 1% to about 20% by weight of the blend.

17. The preform of claim 15 wherein the at least one first composition ceramic powder is from about 80% to about 99% by weight of the blend.

18. The preform of claim 1 wherein neither the insert nor the first composition is a wrought portion.

19. The preform of claim 1 wherein the binder is selected from the group consisting of acetal, polyethylene, polypropylene, polyethylene glycol, polyalkylene glycol, paraffin wax, oleic acid, polysaccharide (agar), naphthalene or paradichlorobenzene or combinations thereof, and combinations thereof.

20. The preform of claim 1 having a complex geometry.

21. The preform of claim 1 configured for use:
a) in a hip replacement assembly, the preform being selected from the group consisting of a acetabular shell, a femoral head, and a femoral stem;
b) in a knee replacement assembly, the preform being selected from the group consisting of a femoral component and a tibial tray;
c) in a shoulder replacement assembly, the preform being selected from the group consisting of a humeral stem, a glenoid sphere, and a glenoid fixation device;
d) as a lumbar fixation device;
e) as an orthopedic screw;
f) as a vertebral disc replacement device; and
g) in a spinal fixation assembly.

22. The preform of claim 1 wherein the insert has a second composition that is different than the first composition.

23. A brown metal, a brown ceramic, or a brown metal and ceramic preform, the preform comprising:
a) a plurality of inserts, each insert of an insert metal powder, an insert ceramic powder, or an insert metal and ceramic powder mixture, wherein at least two of the plurality of inserts are of different insert compositions of the insert metal powder, the insert ceramic powder, or the insert metal and ceramic powder mixture; and
b) a first composition surrounding the plurality of inserts, the first composition comprising:
  i) a composition metal powder, a composition ceramic powder, or a combination of composition metal and composition ceramic powders; and
  ii) a binder comprising a carrier component,
c) wherein at least the first composition has a microstructure that includes micro voids and interstitial paths characteristic of the carrier component having been volatilized from the binder; and
d) wherein the micro voids of the first composition have a micro void size that is about 1-10 times a particle size of the first composition metal powder, the first composition ceramic powder, or the combination of the first composition metal and ceramic powders.

24. The preform of claim 23 configured for use as or in a medical device.

25. The preform of claim 23 wherein the insert comprise an insert metal powder, an insert ceramic powder, or an insert metal and ceramic powder mixture.

26. The preform of claim 23 wherein, after sintering and then forging, at least the first composition has a density that is at least 98% of the first composition's theoretical density prior to being sintered.

27. The preform of claim 23 wherein the insert is relatively less dense than the surrounding first composition.

28. The preform of claim 23 wherein at least the first composition comprises a biocompatible first composition metal selected from the group consisting of a cobalt alloy, titanium, a titanium alloy, and a stainless steel alloy.

29. The preform of claim 23 having a length greater than 4 inches along any dimension.

30. The preform of claim 23 being of a size sufficient to contain a 12 mm diameter sphere.

31. The preform of claim 23 having a thickness greater than 12 mm.

32. The preform of claim 23 wherein the at least one insert is a green state insert.

33. The preform of claim 23 wherein the at least one insert is a brown state insert.

34. The preform of claim 23 wherein the at least one insert is both a green state and a brown state insert.

35. The preform of claim 23 wherein the first composition comprises at least one first composition metal powder having particles from about 2 microns to about 150 microns in size.

36. The preform of claim 35 wherein the at least one first composition metal powder has particles from about 25 microns to about 150 microns in size.

37. The preform of claim 23 wherein the first composition metal powder is selected from the group consisting of: a cobalt alloy, a titanium or titanium alloy and a stainless steel.

38. The preform of claim 23 wherein the first composition comprises a blend of at least one first composition metal powder and at least one first composition ceramic powder.

39. The preform of claim 38 wherein the at least one first composition ceramic powder is from about 1% to about 20% by weight of the blend.

40. The preform of claim 38 wherein the at least one first composition ceramic powder is from about 80% to about 99% by weight of the blend.

41. The preform of claim 23 wherein neither the insert nor the first composition is a wrought portion.

42. The preform of claim 23 wherein the binder is selected from the group consisting of acetal, polyethylene, polypropylene, polyethylene glycol, polyalkylene glycol, paraffin wax, oleic acid, polysaccharide (agar), naphthalene or paradichlorobenzene or combinations thereof, and combinations thereof.

43. The preform of claim 23 having a complex geometry.

44. The preform of claim 23 configured for use:
a) in a hip replacement assembly, the preform being selected from the group consisting of a acetabular shell, a femoral head, and a femoral stem;
b) in a knee replacement assembly, the preform being selected from the group consisting of a femoral component and a tibial tray;
c) in a shoulder replacement assembly, the preform being selected from the group consisting of a humeral stem, a glenoid sphere, and a glenoid fixation device;
d) as a lumbar fixation device;
e) as an orthopedic screw;
f) as a vertebral disc replacement device; and
g) in a spinal fixation assembly.

45. The preform of claim 23 wherein the insert has a second composition that is different than the first composition.

46. A brown metal, a brown ceramic, or a brown metal and ceramic preform, the preform comprising:
a) a plurality of inserts, each insert of the same insert metal powder, insert ceramic powder, or insert metal and ceramic powder mixture, wherein at least two of the plurality of inserts are of different particles sizes of the insert metal powder, the insert ceramic powder, or the insert metal and ceramic powders; and
b) a first composition surrounding the plurality of inserts, the first composition comprising:
  i) a composition metal powder, a composition ceramic powder, or a combination of composition metal and ceramic powders; and
  ii) a binder comprising a carrier component,
c) wherein at least the first composition has a microstructure that includes micro voids and interstitial paths characteristic of the carrier component having been volatilized from the binder; and
d) wherein the micro voids of the first composition have a micro void size that is about 1-10 times a particle size of the first composition metal powder, the first composition ceramic powder, or the first composition metal and ceramic powders.

47. The preform of claim 46 configured for use as or in a medical device.

48. The preform of claim 46 wherein the insert comprise an insert metal powder, an insert ceramic powder, or an insert metal and ceramic powder mixture.

49. The preform of claim 46 wherein, after sintering and then forging, at least the first composition has a density that is at least 98% of the first composition's theoretical density prior to being sintered.

50. The preform of claim 46 wherein the insert is relatively less dense than the surrounding first composition.

51. The preform of claim 46 wherein at least the first composition comprises a biocompatible first composition metal selected from the group consisting of a cobalt alloy, titanium, a titanium alloy, and a stainless steel alloy.

52. The preform of claim 46 having a length greater than 4 inches along any dimension.

53. The preform of claim 46 being of a size sufficient to contain a 12 mm diameter sphere.

54. The preform of claim 46 having a thickness greater than 12 mm.

55. The preform of claim 46 wherein the at least one insert is a green state insert.

56. The preform of claim 46 wherein the at least one insert is a brown state insert.

57. The preform of claim 46 wherein the at least one insert is both a green state and a brown state insert.

58. The preform of claim 46 wherein the first composition comprises at least one first composition metal powder having particles from about 2 microns to about 150 microns in size.

59. The preform of claim 58 wherein the at least one first composition metal powder has particles from about 25 microns to about 150 microns in size.

60. The preform of claim 46 wherein the first composition metal powder is selected from the group consisting of: a cobalt alloy, a titanium or titanium alloy and a stainless steel.

61. The preform of claim 46 wherein the first composition comprises a blend of at least one first composition metal powder and at least one first composition ceramic powder.

62. The preform of claim 61 wherein the at least one first composition ceramic powder is from about 1% to about 20% by weight of the blend.

63. The preform of claim 62 wherein the at least one first composition ceramic powder is from about 80% to about 99% by weight of the blend.

64. The preform of claim 46 wherein neither the insert nor the first composition is a wrought portion.

65. The preform of claim 46 wherein the binder is selected from the group consisting of acetal, polyethylene, polypropylene, polyethylene glycol, polyalkylene glycol, paraffin wax, oleic acid, polysaccharide (agar), naphthalene or paradichlorobenzene or combinations thereof, and combinations thereof.

66. The preform of claim 46 having a complex geometry.

67. The preform of claim 46 configured for use:
a) in a hip replacement assembly, the preform being selected from the group consisting of a acetabular shell, a femoral head, and a femoral stem;
b) in a knee replacement assembly, the preform being selected from the group consisting of a femoral component and a tibial tray;
c) in a shoulder replacement assembly, the preform being selected from the group consisting of a humeral stem, a glenoid sphere, and a glenoid fixation device;
d) as a lumbar fixation device;
e) as an orthopedic screw;
f) as a vertebral disc replacement device; and
g) in a spinal fixation assembly.

68. The preform of claim 46 wherein the insert has a second composition that is different than the first composition.

69. A brown metal, a brown ceramic, or a brown metal and ceramic preform, the preform comprising:
a) at least one insert; and
b) a first composition surrounding the at least one insert, the first composition comprising:
i) a first composition metal powder, a first composition ceramic powder, or a combination of the first composition metal and ceramic powders; and
ii) a binder comprising a carrier component,
c) wherein at least the first composition has a microstructure that includes micro voids and interstitial paths, the interstitial paths residing between and connecting to adjacent micro voids, and
d) wherein the micro voids of the first composition have a micro void size that is about 1-10 times a particle size of the first composition metal powder, the first composition ceramic powder, or the combination of the first composition metal and ceramic powders.

70. The preform of claim 69 wherein the at least one first composition ceramic powder is from about 1% to about 20% by weight of the blend.

71. The preform of claim 69 wherein the at least one first composition ceramic powder is from about 80% to about 99% by weight of the blend.

72. The preform of claim 69 wherein the at least one insert is a green state insert.

73. The preform of claim 69 wherein the at least one insert is a brown state insert.

74. The preform of claim 69 wherein the at least one insert is both a green state and a brown state insert.

* * * * *